US012295564B2

(12) United States Patent
Breslich et al.

(10) Patent No.: US 12,295,564 B2
(45) Date of Patent: May 13, 2025

(54) SELF-DRILLING ANCHOR INSERTER

(71) Applicant: Conmed Corporation, Utica, NY (US)

(72) Inventors: Grady Breslich, Saint Petersburg, FL (US); Peter Miller, Largo, FL (US); James M. Barber, Largo, FL (US); Bennie Wayne Gladdish, Jr., Odessa, FL (US)

(73) Assignee: Conmed Corporation, Utica, NY (US)

( * ) Notice: Subject to any disclaimer, the term of this patent is extended or adjusted under 35 U.S.C. 154(b) by 811 days.

(21) Appl. No.: 17/414,681

(22) PCT Filed: Dec. 18, 2019

(86) PCT No.: PCT/US2019/067142
§ 371 (c)(1),
(2) Date: Jun. 16, 2021

(87) PCT Pub. No.: WO2020/132049
PCT Pub. Date: Jun. 25, 2020

(65) Prior Publication Data
US 2022/0015753 A1 Jan. 20, 2022

Related U.S. Application Data

(60) Provisional application No. 62/781,246, filed on Dec. 18, 2018.

(51) Int. Cl.
*A61B 17/04* (2006.01)
*A61B 17/16* (2006.01)
*A61B 17/17* (2006.01)

(52) U.S. Cl.
CPC ...... *A61B 17/0401* (2013.01); *A61B 17/1615* (2013.01); *A61B 2017/0409* (2013.01); *A61B 17/1624* (2013.01); *A61B 17/17* (2013.01)

(58) Field of Classification Search
CPC ............ A61B 17/0401; A61B 17/1615; A61B 17/1624; A61B 17/17; A61B 2017/0409;
(Continued)

(56) References Cited

U.S. PATENT DOCUMENTS 5,411,523 A 5/1995 Goble
5,441,502 A * 8/1995 Bartlett ................. A61F 2/0811
606/104

(Continued)

FOREIGN PATENT DOCUMENTS

WO 01/54586 8/2001
WO 2013/120004 8/2013
(Continued)

OTHER PUBLICATIONS

International Search Report Form PCT/ISA/210, International Application No. PCT/US2018/043446, pp. 1-19 Dated, Nov. 6, 2018.
(Continued)

*Primary Examiner* — Mohamed G Gabr
*Assistant Examiner* — Aman Kumar Mann
(74) *Attorney, Agent, or Firm* — Bond, Schoeneck & King, PLLC; Frederick J. M. Price

(57) ABSTRACT

An anchor inserter including an inserter tube extending along a longitudinal axis having a proximal inserter end and a distal inserter end. The inserter also includes an inserter tip attached to and extending distally from the distal inserter end. The inserter tip has a proximal tip end and a distal tip end with a suture anchor retention slot extending through the distal tip end. The inserter has one or more cutting edges extending at least a partially along an outer perimeter edge of the distal tip end. The distal tip end has a first arm and a second arm. The first arm is substantially straight and the second arm is curved.

12 Claims, 60 Drawing Sheets

(58) Field of Classification Search
CPC ...... A61B 17/1622; A61B 2017/00473; A61B 2017/0406; A61B 17/1796; A61B 17/3421; A61B 2017/0403; A61B 2017/0445

See application file for complete search history.

(56) References Cited

U.S. PATENT DOCUMENTS

| | | | |
|---|---|---|---|
| 5,591,207 | A | 1/1997 | Coleman |
| 5,851,219 | A | 12/1998 | Goble et al. |
| 5,904,704 | A | 5/1999 | Goble et al. |
| 6,156,039 | A | 12/2000 | Thal |
| 6,626,916 | B1 | 9/2003 | Yeung et al. |
| 7,025,770 | B2 | 4/2006 | McGuire et al. |
| 7,041,120 | B2 | 5/2006 | Li et al. |
| 7,381,213 | B2 * | 6/2008 | Lizardi ............... A61B 17/0401 606/68 |
| 7,749,250 | B2 | 7/2010 | Stone et al. |
| 8,202,318 | B2 | 6/2012 | Willobee |
| 8,273,106 | B2 | 9/2012 | Stone et al. |
| 8,591,545 | B2 | 11/2013 | Lunn et al. |
| 8,795,334 | B2 | 8/2014 | Astorino et al. |
| 9,044,224 | B2 | 6/2015 | Lauria |
| 9,084,597 | B2 | 7/2015 | Arai et al. |
| 9,173,652 | B2 | 11/2015 | Lombardo et al. |
| 9,320,512 | B2 | 4/2016 | Dooney, Jr. |
| 9,370,352 | B2 | 6/2016 | Astorino et al. |
| 9,421,010 | B2 | 8/2016 | Dreyfuss |
| 9,445,803 | B2 | 9/2016 | Marchand et al. |
| 9,585,654 | B2 | 3/2017 | Dean et al. |
| 9,610,074 | B2 | 4/2017 | Martin |
| 9,750,492 | B2 * | 9/2017 | Ziniti ................ A61B 17/0487 |
| 9,820,731 | B2 | 11/2017 | Arai et al. |
| 9,826,971 | B2 | 11/2017 | Lombardo et al. |
| 10,092,284 | B2 | 10/2018 | Bouduban et al. |
| 10,182,806 | B2 | 1/2019 | Foerster |
| 10,258,326 | B2 | 4/2019 | Sung |
| 10,383,619 | B2 | 8/2019 | Thal |
| 10,448,944 | B2 | 10/2019 | Marchand et al. |
| 10,568,616 | B2 | 2/2020 | Monllor et al. |
| 10,631,844 | B2 | 4/2020 | Astorino et al. |
| 10,687,798 | B2 | 6/2020 | Lombardo et al. |
| 10,722,343 | B2 | 7/2020 | Pilgeram et al. |
| 2005/0240199 | A1 * | 10/2005 | Martinek ............. A61B 17/062 606/104 |
| 2007/0142835 | A1 * | 6/2007 | Green ................ A61B 17/0483 606/232 |
| 2008/0140092 | A1 * | 6/2008 | Stone ................ A61B 17/0469 606/139 |
| 2009/0318959 | A1 * | 12/2009 | Burkhart ............ A61B 17/0401 606/228 |
| 2010/0298872 | A1 | 11/2010 | Berndt et al. |
| 2011/0054524 | A1 | 3/2011 | Beevers et al. |
| 2011/0276137 | A1 | 11/2011 | Seedhom et al. |
| 2013/0018416 | A1 | 1/2013 | Lombardo et al. |
| 2013/0144334 | A1 * | 6/2013 | Bouduban .......... A61B 17/0401 606/232 |
| 2013/0237997 | A1 | 9/2013 | Arai et al. |
| 2013/0267998 | A1 * | 10/2013 | Vijay ................ A61B 17/0401 606/232 |
| 2013/0345751 | A1 | 12/2013 | Beck |
| 2014/0257383 | A1 * | 9/2014 | Lombardo .......... A61B 17/0401 606/232 |
| 2015/0032155 | A1 | 1/2015 | Dreyfuss et al. |
| 2015/0066079 | A1 | 3/2015 | Schmieding |
| 2015/0272566 | A1 * | 10/2015 | Arai .................. A61B 17/0401 606/232 |
| 2016/0030159 | A1 * | 2/2016 | Ticker ................ A61F 2/0811 606/232 |
| 2016/0157844 | A1 | 6/2016 | Guy |
| 2016/0270777 | A1 | 9/2016 | Miller et al. |
| 2016/0296223 | A1 * | 10/2016 | Monllor ............. A61B 17/0401 |
| 2017/0055975 | A1 | 3/2017 | Thal |
| 2017/0071590 | A1 | 3/2017 | Macleod |
| 2017/0156727 | A1 | 6/2017 | Wilson-Wirth et al. |
| 2017/0181739 | A1 | 6/2017 | Breslich |
| 2017/0252031 | A1 | 9/2017 | Harari et al. |
| 2017/0354430 | A1 * | 12/2017 | Beeby ................ A61B 17/3468 |
| 2018/0049734 | A1 | 2/2018 | Kam |
| 2018/0235746 | A1 | 8/2018 | Pilgeram et al. |
| 2018/0256150 | A1 * | 9/2018 | Gustafson .......... A61B 17/0401 |
| 2018/0271514 | A1 * | 9/2018 | Burkhart ............ A61B 17/0401 |
| 2018/0296207 | A1 | 10/2018 | Burkhart et al. |
| 2018/0303475 | A1 * | 10/2018 | Sengun .............. A61B 17/0401 |
| 2019/0059875 | A1 * | 2/2019 | Srikumaran ....... A61B 17/1604 |

FOREIGN PATENT DOCUMENTS

| | | |
|---|---|---|
| WO | 2016/154099 | 9/2016 |
| WO | 2017/117100 | 7/2017 |
| WO | 2017/139132 | 8/2017 |
| WO | 2018/035232 | 2/2018 |

OTHER PUBLICATIONS

International Search Report Form PCT/ISA/210, International Application No. PCT/US2019/067142, pp. 1-14 Dated, Apr. 14, 2020.
Translated Japanese Office Action, Dated Dec. 5, 2022, Mailed on Dec. 13, 2022, Japanese Patent Application No. 2021-534748, entire document.
KR Office Action, Application No. 10-2021-7021127, dated Nov. 27, 2023, entire document.
"CN First Office Action, Application No. 201980084695.7, dated Jun. 28, 2024, entire document".

* cited by examiner

SELF-DRILLING ANCHOR INSERTER

CROSS-REFERENCES TO RELATED APPLICATIONS

The present application is a national stage application under 35 U.S.C. 371 based on international patent application PCT/US19/67142 filed on Dec. 18, 2019, which claims priority to and the benefit of U.S. Provisional Patent Application No. 62/781,246, filed on Dec. 18, 2018 and entitled "Self-Drilling Anchor Inserter," the entireties of which are hereby incorporated herein by reference. The present application relates to U.S. Provisional Patent Application No. 62/572,369 filed on Oct. 13, 2017, U.S. Provisional Patent Application No. 62/618,851, filed on Jan. 18, 2018, U.S. Provisional Patent Application No. 62/631,034, filed on Feb. 15, 2018, U.S. Provisional Patent Application No. 62/543,516, filed on Aug. 10, 2017, U.S. Provisional Patent Application No. 62/536,208, filed on Jul. 24, 2017.

BACKGROUND OF THE INVENTION

1. Field of the Invention

The present invention relates to drills, anchor drivers, and a drill guide for drilling a bone hole at a surgical repair site and inserting a suture anchor in the bone hole and, more particularly, to a self-drilling all-suture anchor and inserter.

2. Description of Related Art

Many orthopedic surgical and medical procedures require the fixation of one body to another body. Such bodies may include bone, soft tissue, and prosthetics. One body can be fixed in a position relative to another using connector devices, such as screws and suture anchors (e.g., cannulated knotless suture anchors and soft all suture anchors). For example, various orthopedic surgeries require the insertion and fixation of a suture anchor within a bone.

One example of a suture anchor is a soft suture anchor, such as the Y-Knot® device. See, e.g., U.S. Pat. No. 9,826,971. Since soft anchors are commonly made entirely of suture materials, they are sometimes called "all-suture" anchors, and generally include a fibrous construct anchor body portion (or fibrous, braided or woven fabric-type structure such as a flexible web, as described in U.S. Pat. No. 9,173,652) and a suture or filament portion. In a traditional Y-Knot device, the suture is pierced entirely through the braid material a number of times, such that the suture passes through a "front" surface and a "back" surface. When a Y-Knot anchor is constructed in the traditional manner, the segments of suture on the back surface of the braid are in contact with bone and can be abraded by the bone due to friction.

There are at least two general, conventional methods for inserting a suture anchor within a bone. In one method, a bone hole is created and prepared using a drill bit. The drill bit is typically advanced through a drill guide to create the bone hole and then, a suture anchor is passed through or down the drill guide into the bone hole for deployment. If the drill guide is moved between creation of the bone hole and advancement of the suture anchor, the drill guide may be moved out of alignment with the bone hole. If the drill guide is no longer aligned with the bone hole, the suture anchor often cannot be inserted and deployed. Therefore, the creation of a second bone hole is often required when drill guide moves out of alignment with the first bone hole.

In a second method, the drilling step is eliminated in an attempt to avoid the aforementioned misalignment issue. A self-punching suture anchor, such as the Y-Knot RC Suture Anchor, for example, is designed with an inserter that allows the anchor in the inserter to be directly positioned on the bone at the desired location. When the anchor in the inserter is positioned at the desired location, the inserter can be hammered, forcing the anchor directly into the bone. However, hammering the anchor into the bone imparts impact forces to the bone which may be undesirable for some surgical site locations. For example, impact forces may be particularly undesirable at the glenoid bone or smaller bones, such as in the extremities. Further, self-punching anchors are generally required to be larger in size. Thus, such anchors may not only be undesirable but unusable in smaller bones.

Therefore, there is a need for a suture anchor inserter that can insert a small suture anchor into the bone without the need to drill a bone hole or to impart impact forces on the bone and which can achieve the minimum hole size that results when an anchor is not contributing to the enlargement of the hole.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention recognize that there are potential problems and/or disadvantages with the conventional methods for drilling a bone hole and inserting a suture anchor (as discussed herein and above). For example, removing a drill bit from the drill guide and replacing it with a driver to insert the suture anchor increases the risk of misalignment of the drill guide with the bone hole, which requires additional surgical time and risks trauma to the surrounding tissue and bone. In another example, hammering the anchor into the bone imparts impact forces to the bone which may be undesirable for some surgical site locations. Therefore, a need exists for a simple-to-use suture anchor inserter that can insert a suture anchor into the bone without the need to drill a bone hole or to impart impact forces on the bone and which can achieve the minimum hole size that results when an anchor is not contributing to the enlargement of the hole. Various embodiments of the present invention may be advantageous in that they may solve or reduce one or more of the potential problems and/or disadvantages discussed herein.

The present disclosure is directed to an inventive configuration, structure, and resulting function of a self-drilling anchor inserter configured to insert suture anchors into bone. According to one aspect, the present invention is an anchor inserter. The anchor inserter includes an inserter tube extending along a longitudinal axis having a proximal inserter end and a distal inserter end. The inserter also includes an inserter tip attached to and extending distally from the distal inserter end. The inserter tip has a proximal tip end and a distal tip end with a suture anchor retention slot extending through the distal tip end. The inserter has one or more cutting edges extending at least a partially along an outer perimeter edge of the distal tip end. The distal tip end has a first arm and a second arm. The first arm is substantially straight and the second arm is curved.

According to another aspect, the present invention is an anchor inserter including a cannulated inserter tube which extends along a longitudinal axis and has a proximal inserter end and distal inserter end. The anchor inserter also includes a cannulated suture tube extending through the cannulated inserter tube. The cannulated suture tube has a proximal suture end and a distal suture end. The anchor inserter further includes an inserter tip attached to and extending distally from the distal inserter end. The inserter tip has a proximal tip end and a distal tip end. One or more features on the proximal tip end are removably connected to one or more features on the distal inserter end.

According to yet another aspect, the present invention is an anchor inserter system further including a cannulated inserter tube extending along a longitudinal axis and having a proximal inserter end and distal inserter end. The system also includes a cannulated suture tube extending through the cannulated inserter tube. The cannulated suture tube has a proximal suture end and a distal suture end. The system further includes an inserter tip attached to and extending distally from the distal inserter end. A suture anchor retention slot extends through the inserter tip and an anchor with a length of suture positioned therethrough extends through the suture anchor retention slot. The length of suture extends proximally along the inserter tip.

Suture material or sutures, as the terms are used and described herein, can include monofilament or multi-filament suture as well as any other metallic or non-metallic filamentary or wire-like material suitable for performing the function of a suture. This material can include both bioabsorbable and non-absorbable materials.

Suture anchors, as the term is used herein, can include soft suture anchors and rigid suture anchors. Soft suture anchors are formed from filaments of suture material which are retained within pre-formed bone holes by being deformable to increase their diameter to a size greater than that of the bone hole, to thereby reside within the cancellous bone and under the bone cortex. One such suture anchor is disclosed in U.S. Pat. No. 9,826,971 assigned to the assignee hereof and incorporated by reference herein in its entirety. Since soft anchors are commonly made entirely of suture materials, they are sometimes called "all-suture" anchors, and generally include a fibrous construct anchor body portion (or fibrous, braided or woven fabric-type structure such as a flexible web, as described in U.S. Pat. No. 9,173,652) and a suture or filament portion. Methods and devices for inserting/deploying such all-suture anchors are known, examples of which are disclosed in U.S. Pat. No. 9,173,652.

As described in U.S. Pat. No. 8,409,252, for example, "non-soft," "hard" or "rigid" suture anchors generally include a "hard" anchor body portion (that may or may not include inner and outer members) and a suture/filament portion. The anchor body of such suture anchors may be formed of a biocompatible and/or bioabsorbable material. These materials may be of such composition that they are reabsorbed by the body, e.g., during the healing process of the bone. Exemplary materials that are suitable for use in the inner and outer members include, but are not limited to, polyetheretherketone ("PEEK"), polylactic acid/beta-tricalcium phosphate ("PLA/Beta-TCP") composites, ultra-high molecular weight polyethylene ("UHMWPE"), as well as other metallic, non-metallic, and polymeric materials.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which.

Figure 32A:
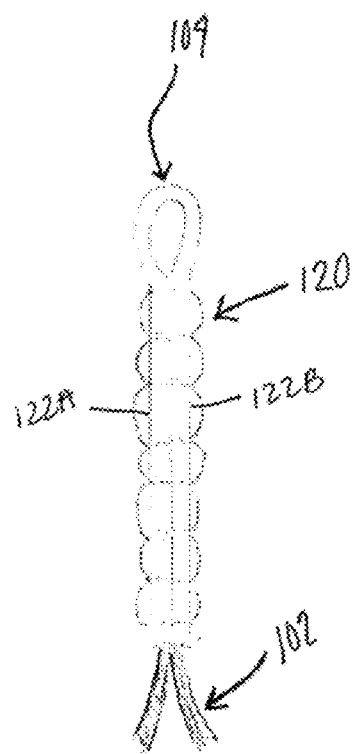
FIG. 32A is a top view schematic representation of an anchor braid folded and stitched, according to an embodiment.
Figure 32B:
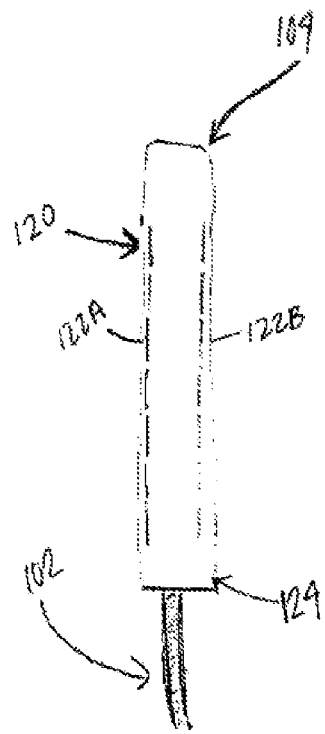
Figure 33:
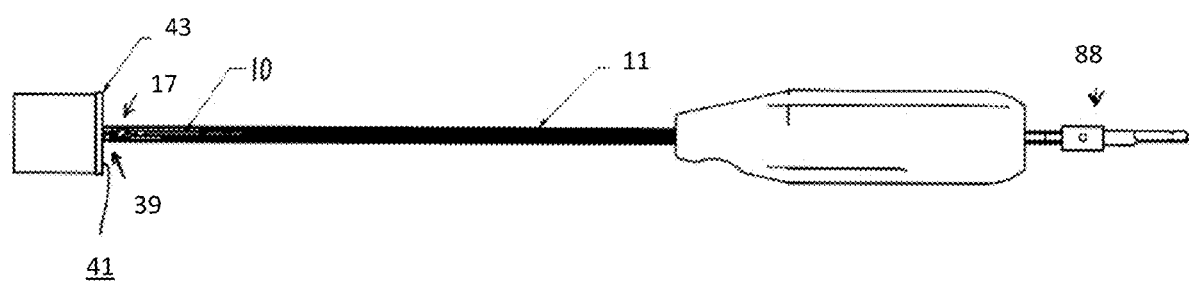
Figure 34:
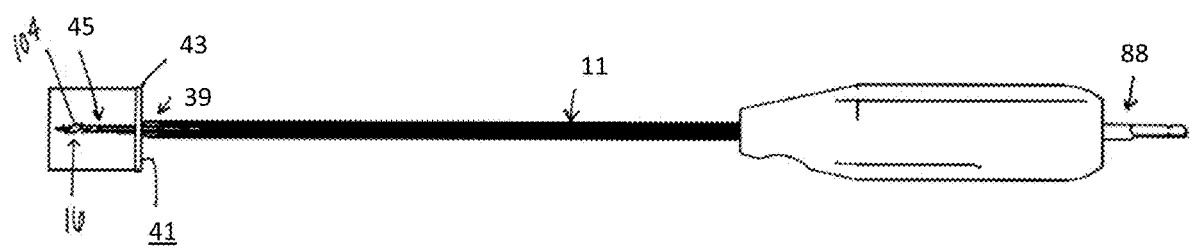
Figure 35:
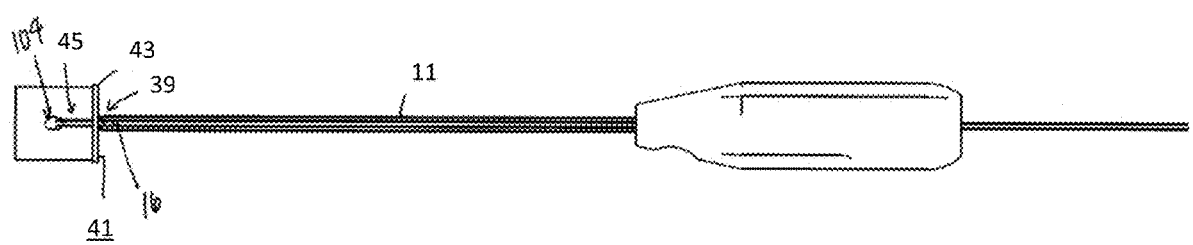
Figure 36A:
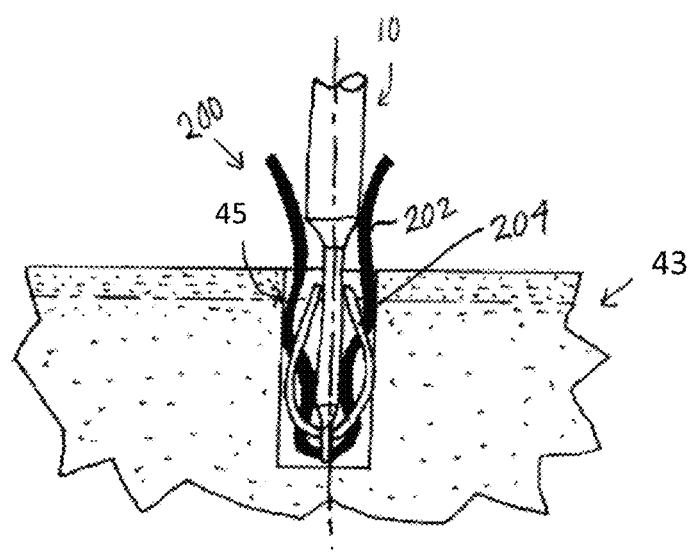
Figure 36B:
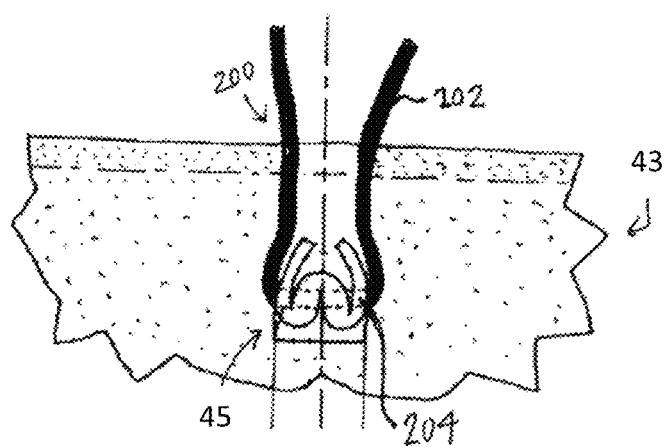
Figure 37:
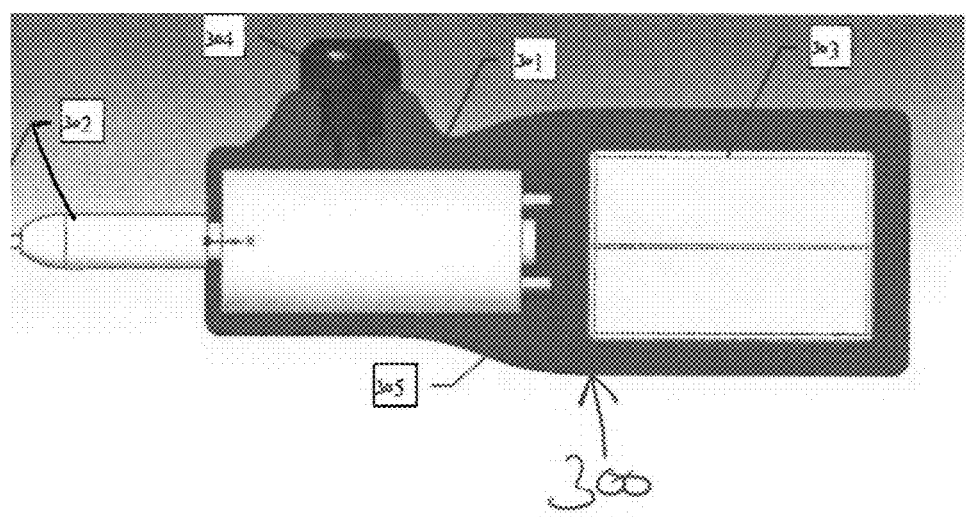
Figure 38:
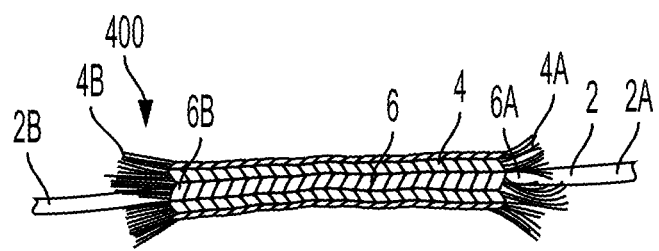
Figure 39A:
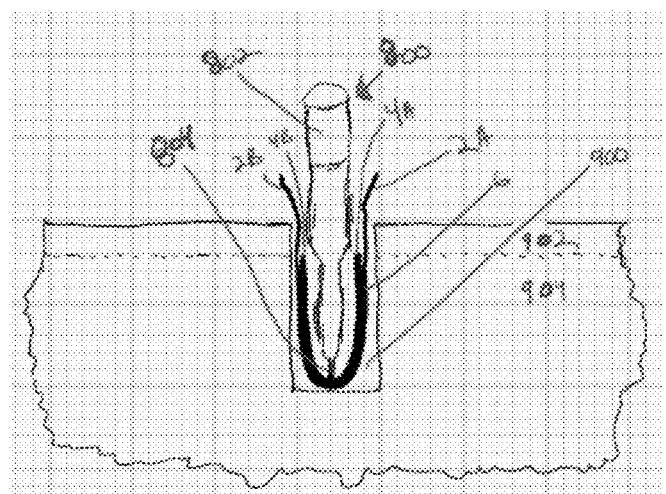
Figure 39B:
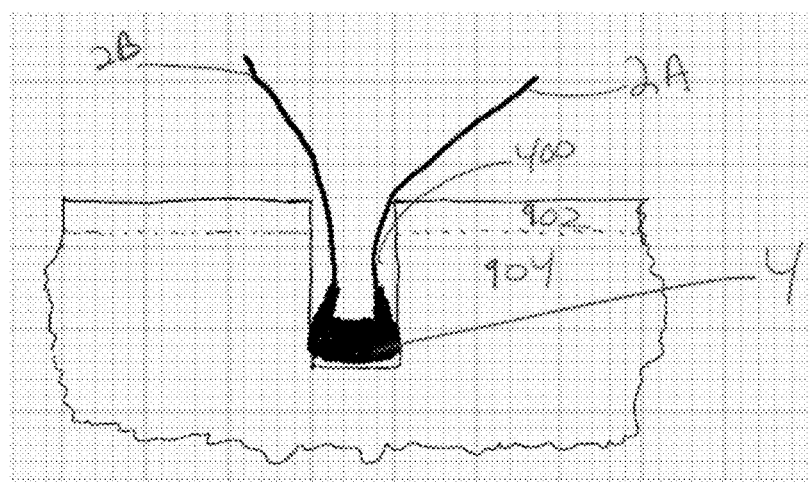
Figure 39C:
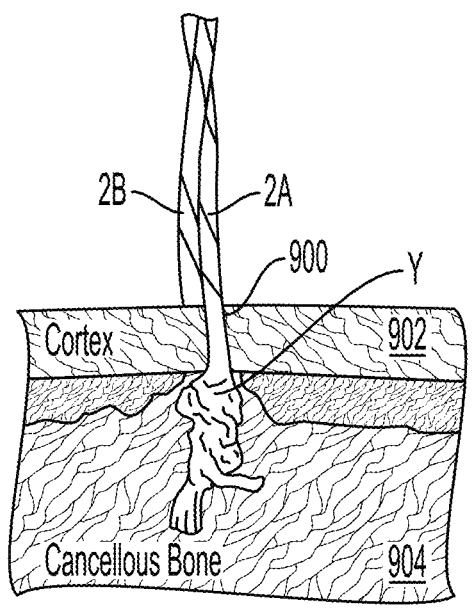
Figure 40:
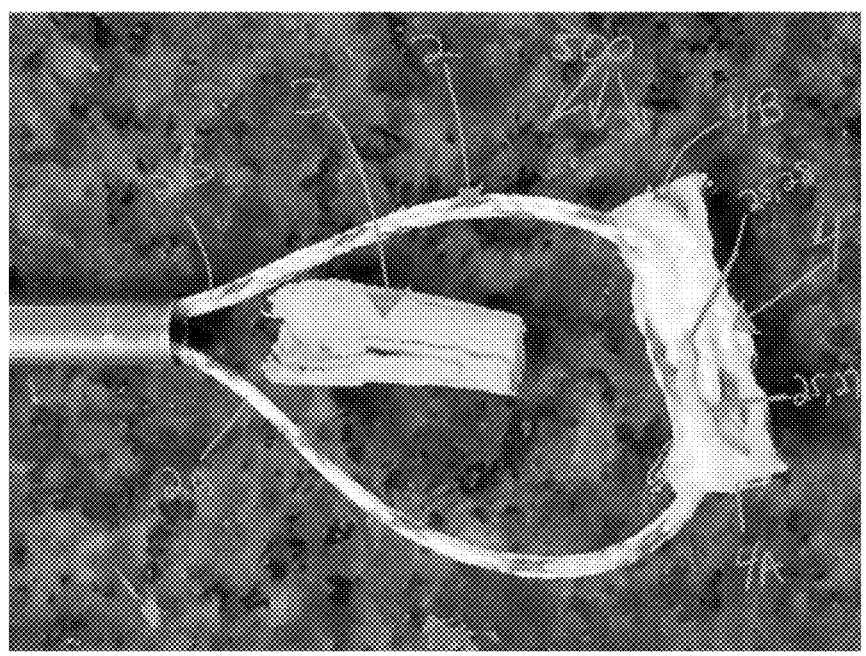
Figure 41A:
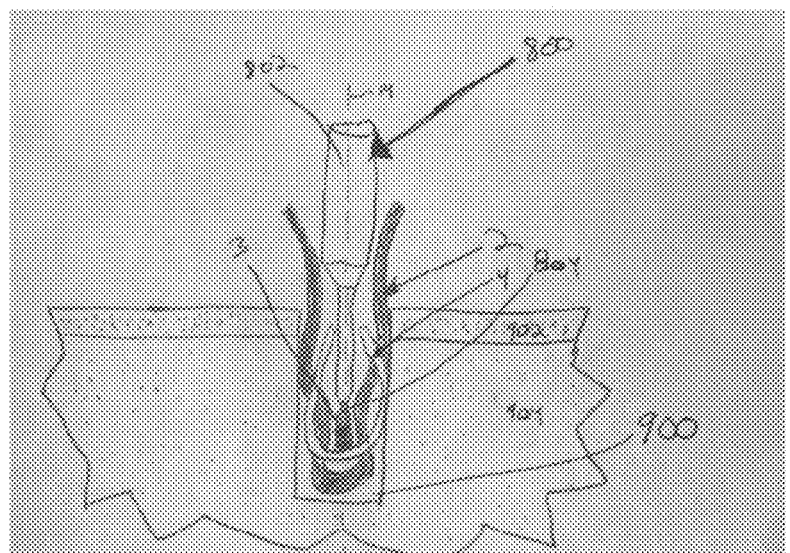
Figure 41B:
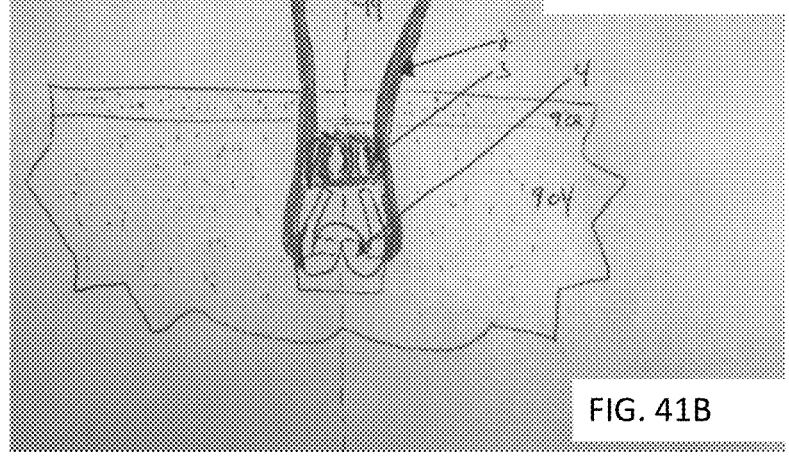
Figure 41C:
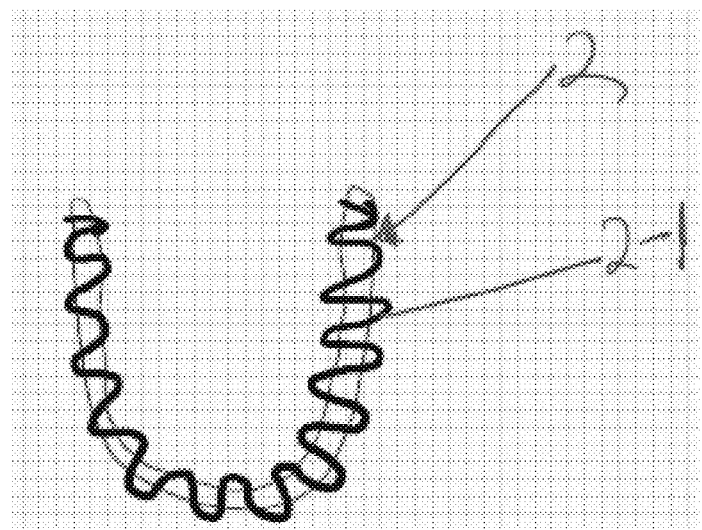
Figure 42:
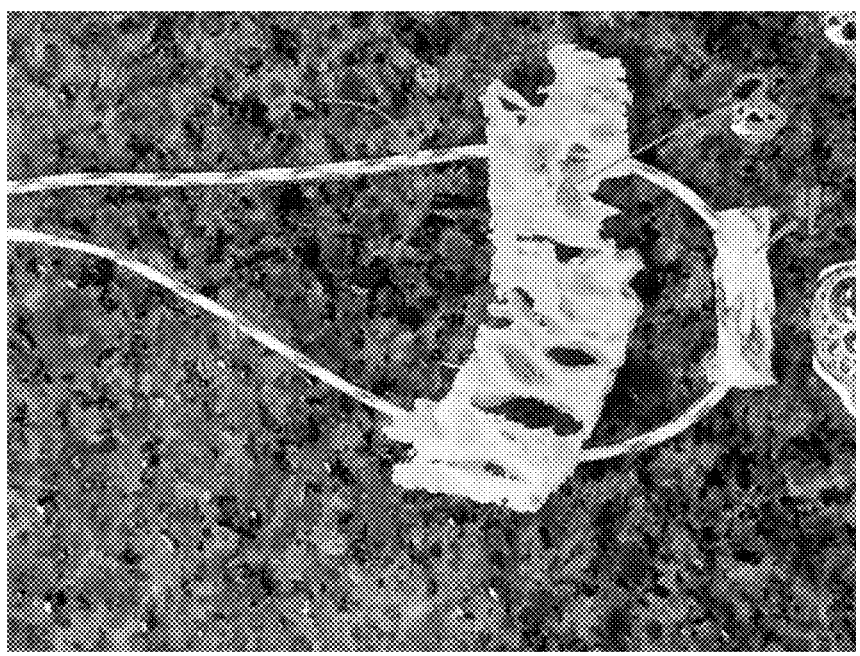
Figure 43:
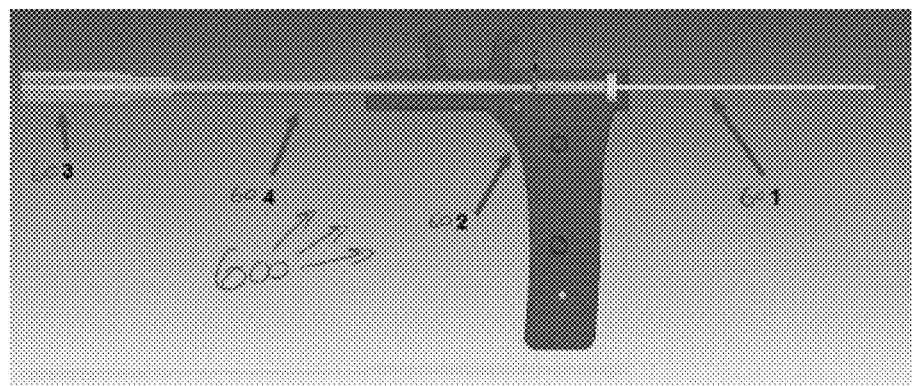
Figure 44:
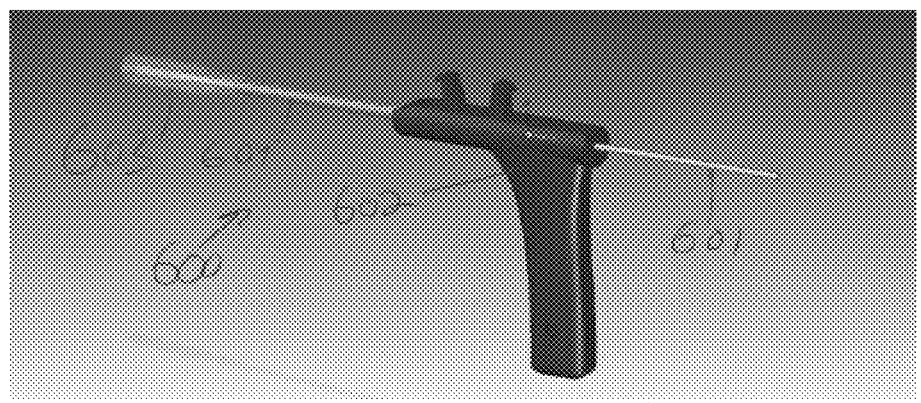
Figure 45:
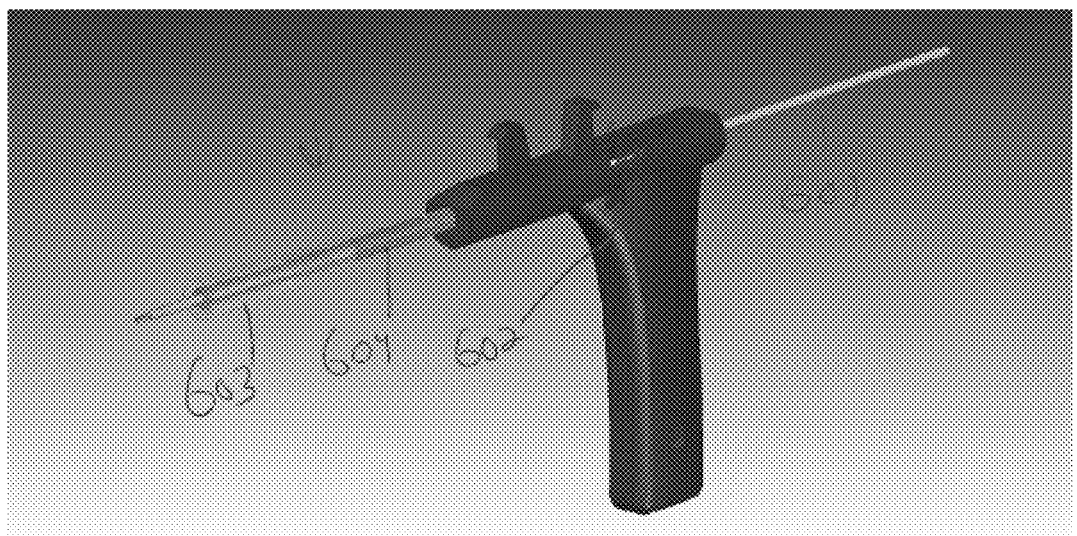

FIG. 32B a top view schematic representation of an anchor braid of FIG. 32A with an additional material covering;

FIG. 33 is a top view schematic representation of the inserter in the unloaded, pre-deployment configuration, according to an alternative embodiment;

FIG. 34 is a top view schematic representation of the inserter in the unloaded, pre-deployment configuration, according to an additional alternative embodiment;

FIG. 35 is a close-up perspective view schematic representation of the distal end of the inserter, according to an embodiment;

FIG. 36A is a side view schematic representation of an embodiment of a suture anchor in the undeployed state, according to an embodiment;

FIG. 36B is a side view schematic representation of the suture anchor of FIG. 36A shortened and expanded in the deployed state, according to an embodiment;

FIG. 37 is a side view schematic representation of a disposable handpiece with a according to an embodiment;

FIG. 38 is a perspective view digital photograph of a soft all-suture anchor in an unloaded (not loaded onto an installation device or inserter), pre-deployment configuration according to an embodiment;

FIG. 39A is a side view schematic representation of an embodiment of the all-suture anchor of FIG. 38 connected to an installation device or inserter in a pre-deployment configuration according to an embodiment FIG. 39B is a side view schematic representation of an embodiment of the all-suture anchor of FIG. 38 in a post-deployment configuration positioned in a bone hole according to an embodiment;

FIG. 39C is a side view digital photograph of an embodiment of the all-suture anchor of FIG. 38 in a post-deployment configuration positioned in a bone hole according to an embodiment;

FIG. 40 is a perspective view digital photograph of a soft all-suture anchor in an unloaded (not loaded onto an installation device or inserter), pre-deployment configuration according to an embodiment;

FIG. 41A is a side view schematic representation of an embodiment of the all-suture anchor of FIG. 40 connected to an installation device or inserter in a pre-deployment configuration according to an embodiment;

FIG. 41B is a side view schematic representation of an embodiment of the all-suture anchor of FIG. 40 in a post-deployment configuration positioned in a bone hole according to an embodiment;

FIG. 41C is a side view schematic representation of a portion of an alternative embodiment of the all-suture anchor according to an embodiment;

FIG. 42 is a side view digital photograph of an embodiment of the all-suture anchor of FIG. 40 in a post-deployment configuration after addition of an activator according to an embodiment;

FIG. 43 is a side view schematic representation of an all-suture anchor insertion device according to an alternative embodiment:

FIG. 44 is a perspective view schematic representation of an all-suture anchor insertion device in a pre-deployed configuration and position according to an alternative embodiment; and FIG. 45 is a perspective view schematic representation of an all-suture anchor insertion device in a pre-deployed configuration and position according to an alternative embodiment.

DETAILED DESCRIPTION OF THE INVENTION

Figure 1:
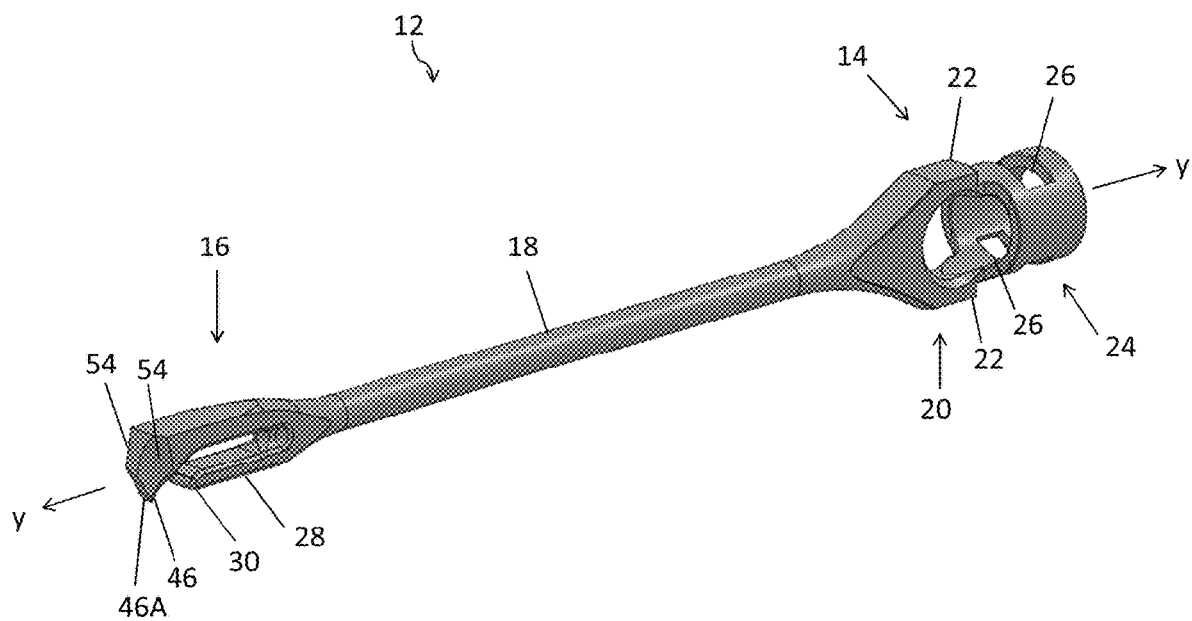
FIG. 1 is a perspective view schematic representation of an inserter tip, according to an embodiment.

Referring now to the drawings, wherein like reference numerals refer to like parts throughout, there is seen a self-drilling anchor inserter 10 (FIG. 11) and its component parts. The inserter 10 comprises an inserter tip 12, shown in FIG. 1. FIG. 1 is a perspective view schematic representation of the inserter tip 12, according to an embodiment. The inserter tip 12 has a proximal tip end 14 and a distal tip end 16 with a shaft 18 extending therebetween. The shaft 18 extends along a central longitudinal y-y axis. In the depicted embodiment, the shaft 18 is solid, although it can be cannulated.

Figure 11:
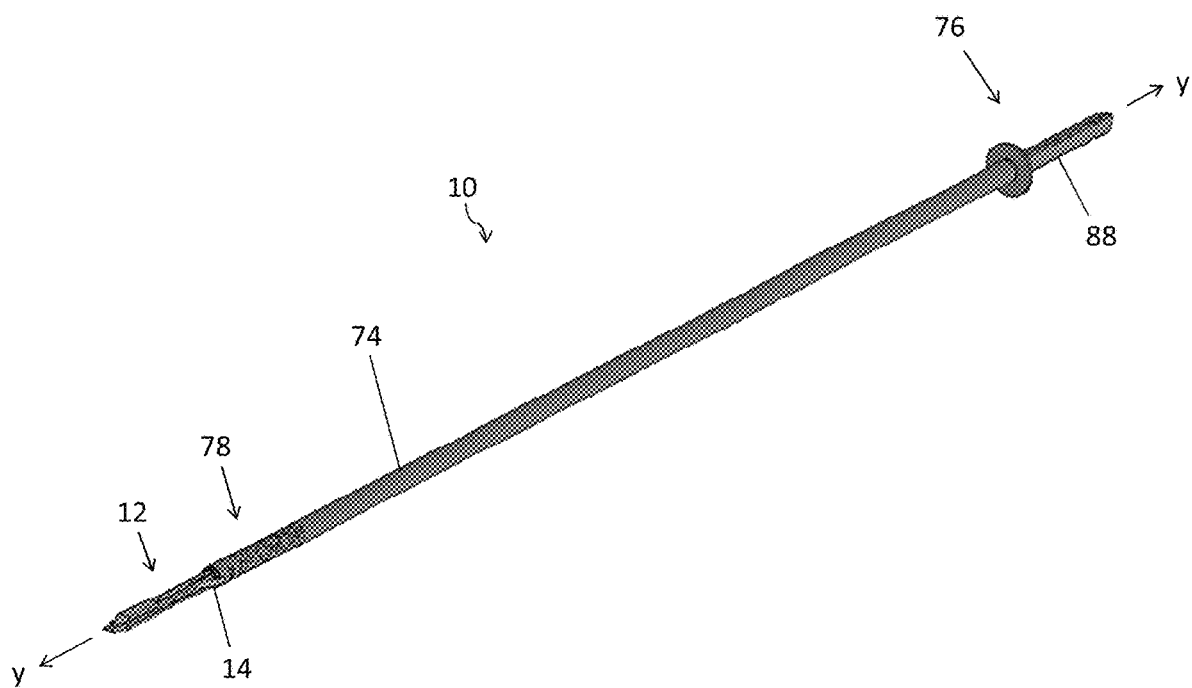
FIG. 11 is a perspective view schematic representation of the self-drilling anchor inserter, according to an embodiment.

The proximal tip end 14 of the inserter tip 12 includes features for connecting the inserter tip 12 to the remainder of the self-drilling anchor inserter 10 (FIG. 11). Specifically, as shown in FIG. 1, the proximal tip end 14 comprises a tip protrusion portion 20. In the depicted embodiment, a cross-section of the tip protrusion portion 20 is substantially triangular. In other words, the tip protrusion portion 20 is tapered such that its diameter or width increases in the proximal direction relative to the central longitudinal y-y axis (or shaft 18). The tip protrusion portion 20 comprises one or more protrusions 22. In the depicted embodiment, the tip protrusion portion 20 comprises two rectangular protrusions 22 which extend in the proximal direction and are spaced such that they are opposing.

Still referring to FIG. 1, the tip protrusion portion 20 is connected to a cannulated, proximal tip tube 24. The proximal tip tube 24 comprises one or more tip recesses 26 extending therethrough. In the depicted embodiment, the proximal tip tube 24 comprises two tip recesses 26 spaced such that they are opposing. As also shown in FIG. 1, the protrusions 22 of the tip protrusion portion 20 are substantially aligned with the recesses 26 of the proximal tip tube 24. The protrusions 22 and the recesses 26 connect to features on the remainder of the self-drilling anchor inserter 10 (FIG. 11), as described in detail below.

Figure 2:
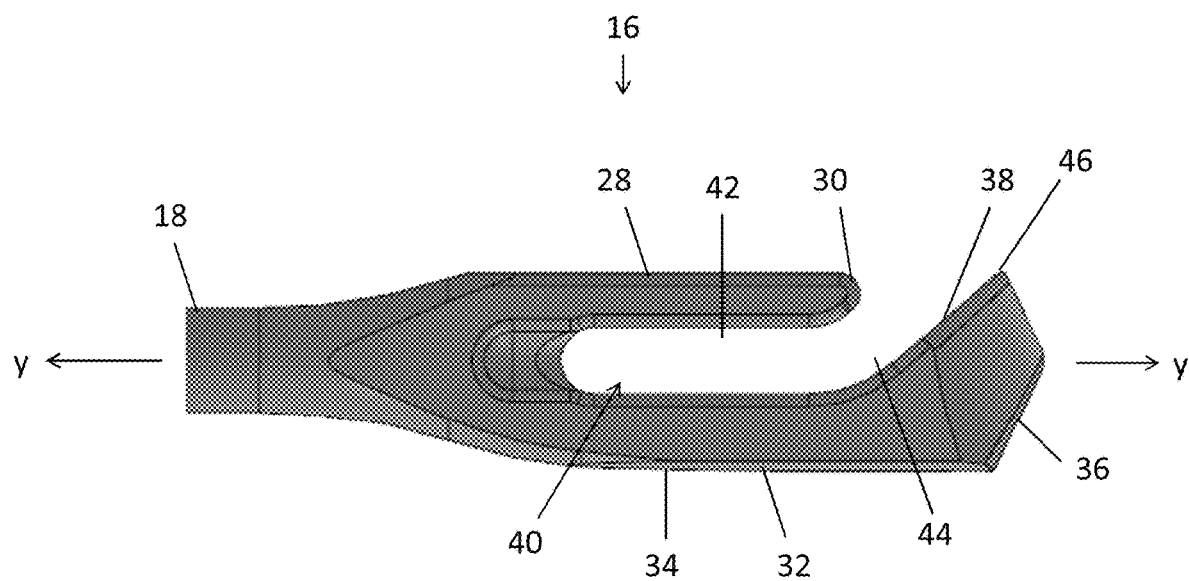
FIG. 2 is a side view schematic representation of a distal tip end of the inserter tip, according to an embodiment.

Turning now to FIG. 2, there is shown a side view schematic representation of a distal tip end 16 of the inserter tip 12, according to an embodiment. The distal tip end 16 of the inserter tip 12 is generally forked (i.e., pronged) or hook-shaped and has a total diameter or width larger than that of the shaft 18. As shown in FIGS. 1 and 2, the distal tip end 16 comprises a first arm 28 extending substantially parallel to the central longitudinal y-y axis in the distal direction. The first arm 28 is substantially straight with a rounded first arm end 30.

The distal tip end 16 also comprises a second arm 32. The second arm 32 is substantially L-shaped, as shown in FIG. 2. The second arm 32 comprises a straight portion 34 that extends substantially parallel to the central longitudinal y-y axis and the first arm 28 in the distal direction. The straight portion 34 of the second arm 32 is connected to a curved portion 36. The curved portion 36 comprises an inner perimeter edge 38 that curves toward the central longitudinal y-y axis such that the inner perimeter edge substantially extends at an angle relative to the central longitudinal y-y axis. Stated differently, the inner perimeter edge 38 of the second arm 32 curves toward an axis extending through the length of the first arm 28.

The configuration of the first arm 28 and the second arm 32 creates a suture anchor retention slot 40 therebetween. The suture anchor retention slot 40 also comprises a straight portion 42 connected to a curved portion 44 that extends at an angle therefrom. The suture anchor retention slot 40 is sized or otherwise configured to hold an anchor braid and length of suture of an all-suture anchor, permitting the all-suture anchor to be pushed into a bone hole by the inserter tip 12.

Figure 3:
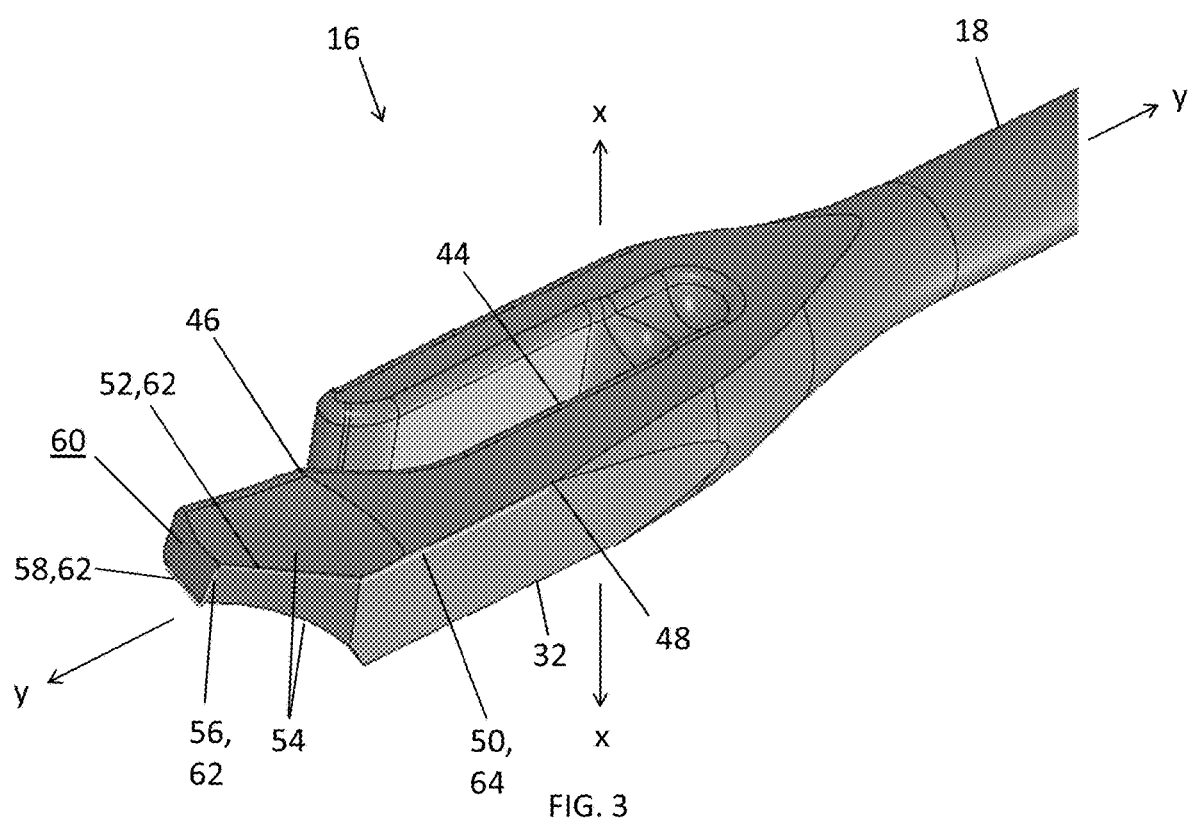
FIG. 3 is a side perspective view schematic representation of the distal tip end of the inserter tip, according to an embodiment.

Referring now to FIG. 3, there is shown a side perspective view schematic representation of the distal tip end 16 of the inserter tip 12, according to an embodiment. The inner perimeter edge 38 of the second arm 32 of the distal tip end 16 extends to a sharp second arm end 46. The second arm end 46 has an edge 46A that extends substantially perpendicular to the central longitudinal y-y axis, as shown in FIG. 1. In FIGS. 1 and 2, the second arm end 46 extends past the first arm end 30 of the first arm 28 to ensure that the first arm end 30 does not have significant contact with the bone during drilling.

The second arm 32 also comprises an outer perimeter edge 48 with an optimized geometry for drilling. As shown in FIG. 3, the outer perimeter edge 48 of the second arm 32 has a straight portion 50 that extends substantially parallel to the central longitudinal y-y axis in the distal direction. The outer perimeter edge 48 also includes an angle portion 52. The angled portion 52 extends at an angle relative to the straight portion 50 (and the central longitudinal y-y axis). In addition, the angled portion 52 extends from the straight portion 50 at angle relative to a lateral x-x axis extending through the suture anchor retention slot 40, as shown.

The configuration of the angled portion 52 is due to a recessed area 54 on the second arm 32. The angled portion 52 extends to a first end portion 56 of the outer perimeter edge 48, as shown in FIG. 3. In the depicted embodiment, the first end portion 56 is substantially perpendicular relative to the straight portion 50. The first end portion 56 connects to a second end portion 58 of the outer perimeter edge 48. The second end portion 58 extends along a z-z axis that is substantially perpendicular to the longitudinal y-y axis and/or the lateral x-x axis. Together, the first and second end portions 56, 58 extend partially around an end surface 60 of the second arm 32.

As shown in FIGS. 1 and 3, the second arm 32 comprises two recessed areas 54, which are corners of the second arm 32 that have been recessed to create multiple cutting edges 62 along the second arm 32. The geometry of the distal tip end 16 creates positive rank angle and clearance angles at the angled portion 52, the first end portion 56, and the second end portion 58. Together, the angled portion 52 and first and second end portions 56, 58 of the outer perimeter edge 48 are cutting edges 62 for effective cutting action. The straight portion 50 of the outer perimeter edge 48 is a reaming edge 64.

Figure 4:
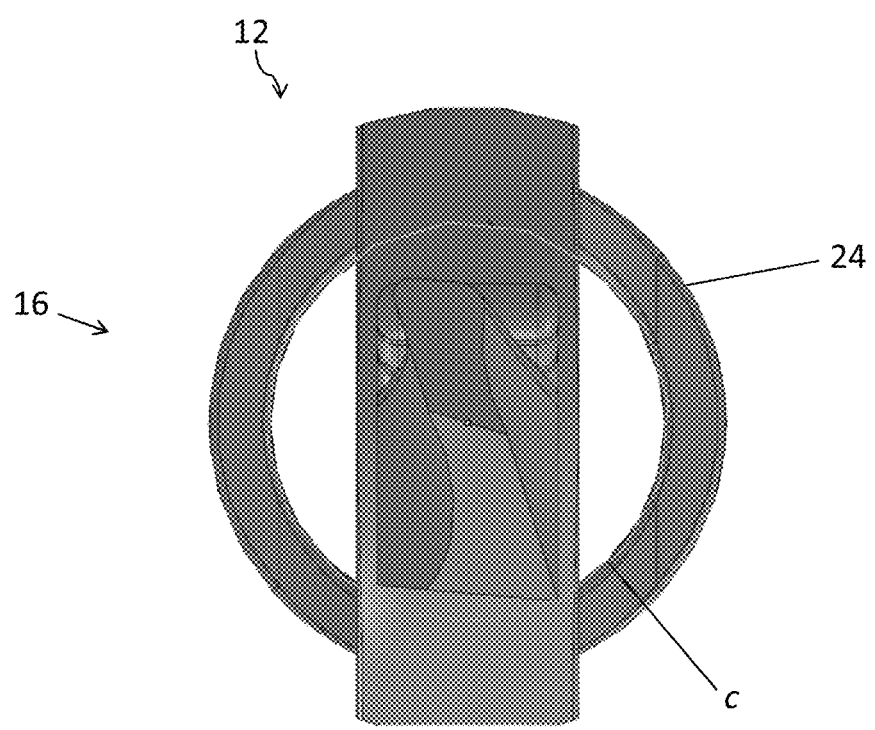
FIG. 4 is a close-up front view schematic representation of the distal tip end of the inserter tip, according to an embodiment.

Turning now to FIG. 4, there is shown a close-up front view schematic representation of the distal tip end 16 of the inserter tip 12, according to an embodiment. In particular, FIG. 4 shows the circumference c of the final hole created by the reaming edge 64 (FIG. 3). The final hole is sized and configured to achieve the minimum hole size that results when an anchor (e.g., anchor braid) is not contributing to the enlargement of the hole.

Figure 5:
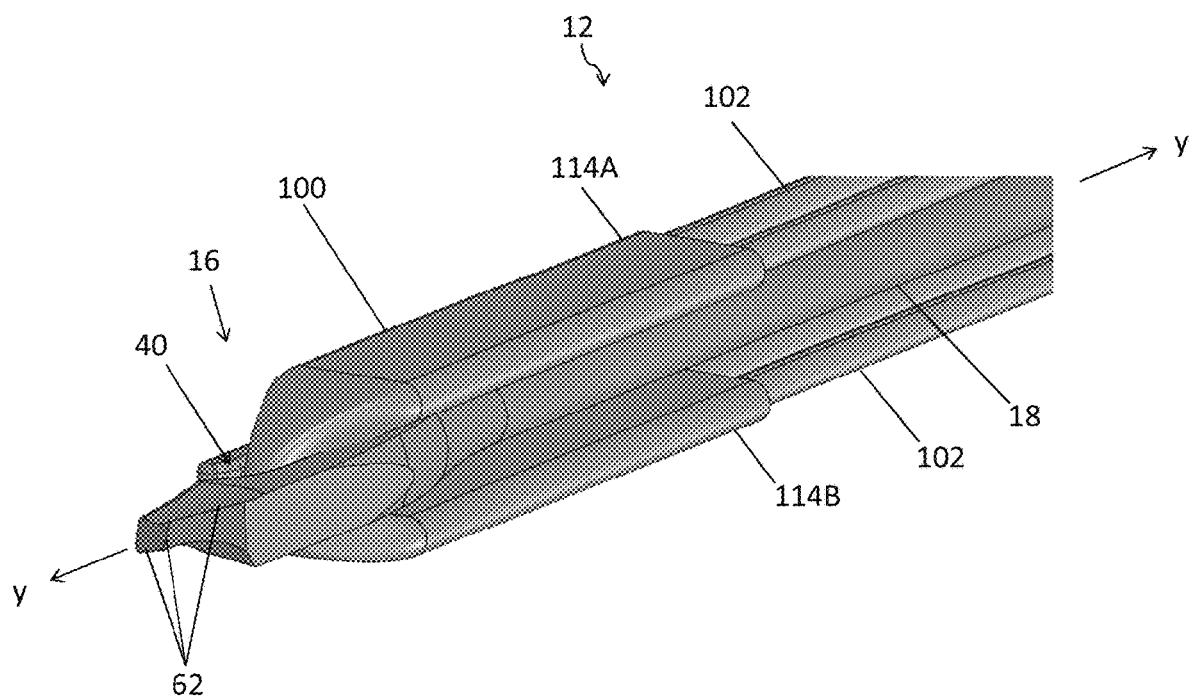
FIG. 5 is a close-up perspective view schematic representation of an anchor positioned within an anchor retention slot of the inserter tip, according to an embodiment.

Referring now to FIG. 5, there is shown a close-up perspective view schematic representation of an anchor 100 positioned within the suture anchor retention slot 40 of the inserter tip 12, according to an embodiment. As shown in FIG. 5, an anchor 100 is positioned or otherwise wrapped within the suture anchor retention slot 40 such that a first end 114A of the anchor 100 and a second end 114B of the anchor 100 extend along opposing sides of the distal tip end 16 and the shaft 18. The anchor 100 is positioned with respect to the cutting edges 62 such that all of the cutting edges 62 are distal relative to the anchor 100. As also shown in FIG. 5, suture 102 is attached to the first and second ends 114A, 114B of the anchor 100. The suture 102 also extends on opposing sides of the distal tip end 16 and the shaft 18.

Figure 6:
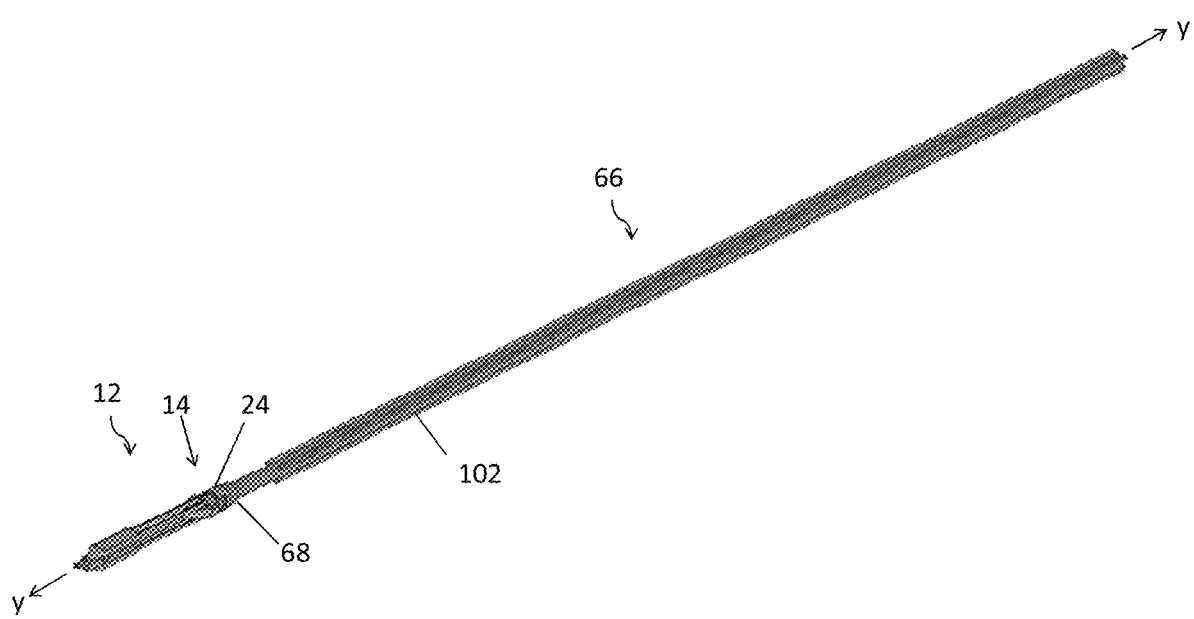
FIG. 6 is a perspective view schematic representation of the inserter tip connected to a suture tube, according to an embodiment.
Figure 13:
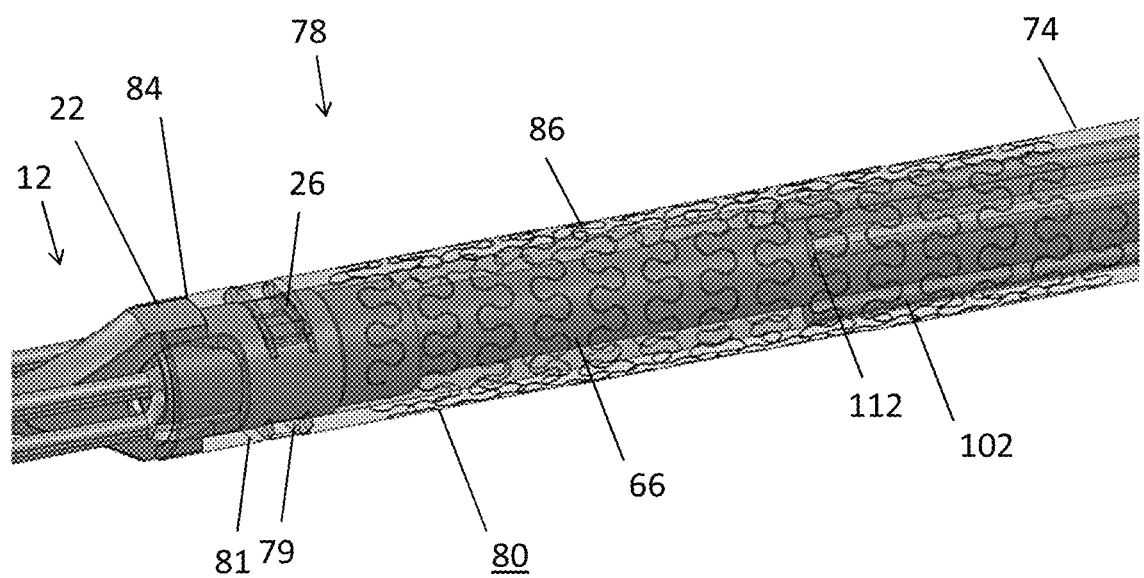
FIG. 13 is a partial transparent perspective view schematic representation of the distal inserter end of the inserter tube connected to the inserter tip, according to an embodiment.

Turning now to FIG. 6, there is shown a perspective view schematic representation of the inserter tip 12 connected to a cannulated suture tube 66, according to an embodiment. As shown, the proximal tip end 14 of the inserter tip 12 connects to the suture tube 66. As described in detail below, the suture tube 66 comprises features that allow the suture 102 connected to the anchor 100 to run through the inserter 10 (FIG. 13). The suture tube 66 comprises a distal suture tube end 68 that is sized and configured to fit within the cannulated proximal tip tube 24 of the inserter tip 12. In other words, an outer diameter of the distal suture tube end 68 is smaller than an inner diameter of the proximal tip tube 24.

Figure 8A:
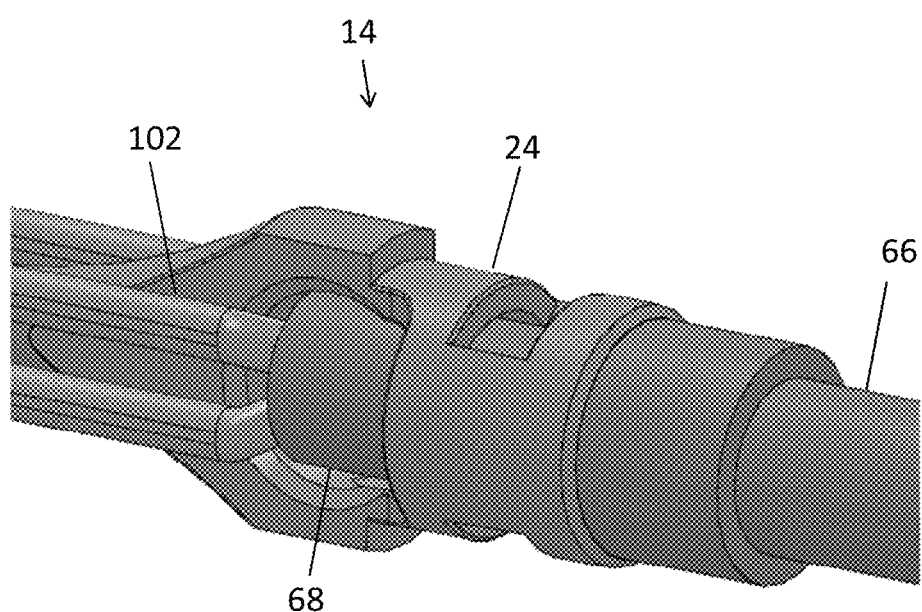
FIG. 8A is a close-up perspective view schematic representation of the inserter tip connected to the suture tube, according to an embodiment.
Figure 8B:
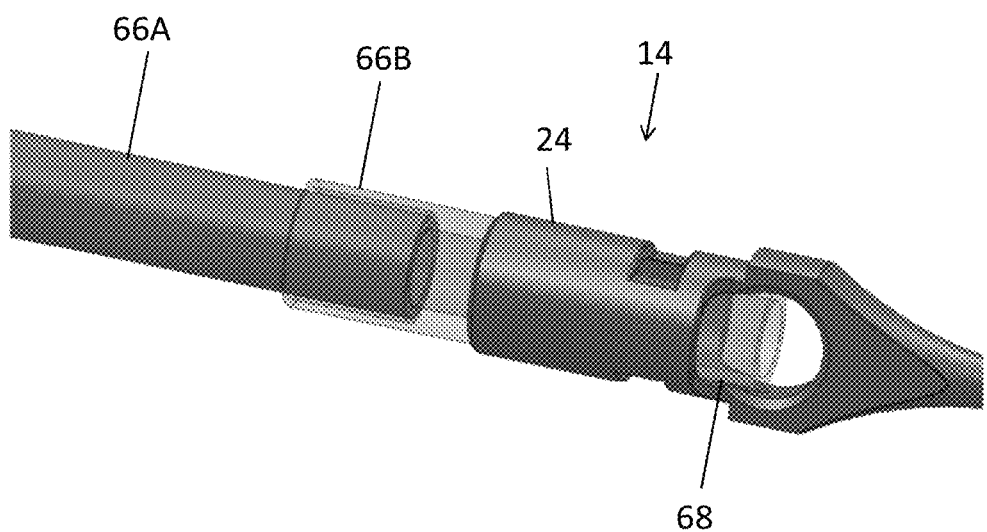
FIG. 8B is a dose-up perspective view schematic representation of the inserter tip connected to the suture tube, according to an alternative embodiment.

In an alternative embodiment shown in FIG. 8B, the suture tube 66 is comprised of two component parts: a first suture tube 66A and a second suture tube 66B. The first suture tube 66A and the second suture tube 66B are cannulated and the second suture tube 66B is sized and configured to fit around the first suture tube 66A. In other words, the first suture tube 66A fits within the second suture tube 66B. As shown in FIG. 8B, the second suture tube 66B connects the first suture tube 66A to the proximal tip end 14 of the inserter tip 12. Specifically, the distal suture tube end 68 (of the second suture tube 66B) extends into the cannulated proximal tip tube 24 of the inserter tip 12. Thus, the first suture tube 66A serves the tubing functionality, while the second suture tube 66B functions as a connector.

Figure 7:
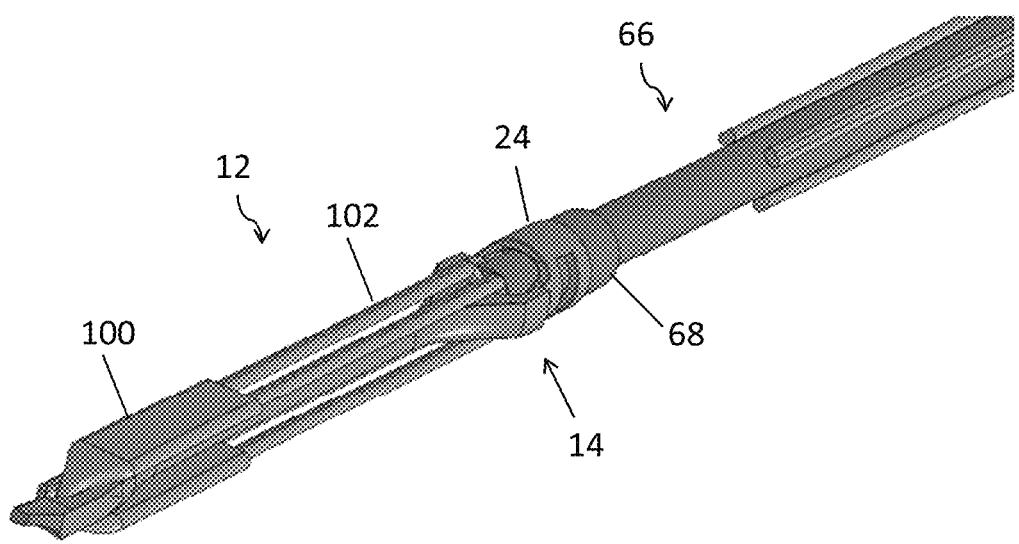
FIG. 7 is a perspective view schematic representation of the a distal suture tube end of the suture tube connected to the inserter tip, according to an embodiment.

Referring now to FIG. 7, there is shown a perspective view schematic representation of the distal suture tube end 68 of the suture tube 66 connected to the inserter tip 12, according to an embodiment. As shown, the suture tube 66 is at least partially within the cannulated proximal tip tube 24. The suture tube 66 does not extend entirely into the proximal tip tube 24. The distal suture tube end 68 and the proximal tip tube 24 comprise features to keep the suture tube 66 from moving farther into the proximal tip tube 24. This is to prevent the distal suture tube end 68 from pinching, compressing, or otherwise interfering with the suture 102. As shown in FIGS. 7 and 8A, the suture 102 extends from the anchor 100 into proximal tip tube 24 and into the distal suture tube end 68 of the cannulated suture tube 66.

Figure 9:
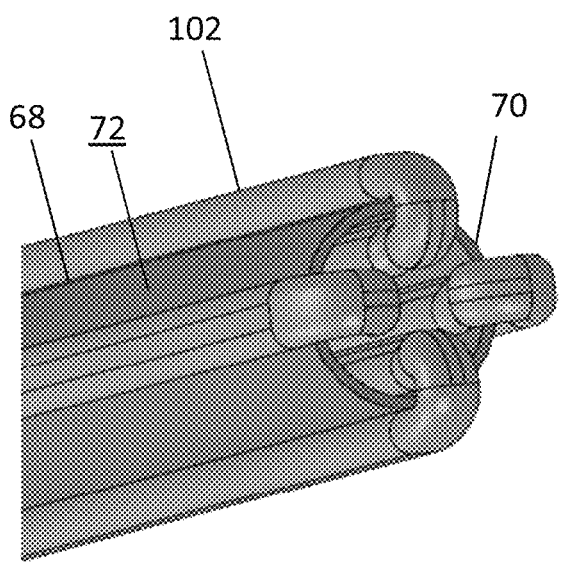
FIG. 9 is a close-up perspective view schematic representation of a proximal suture tube end of the suture tube, according to an embodiment.
Figure 10:
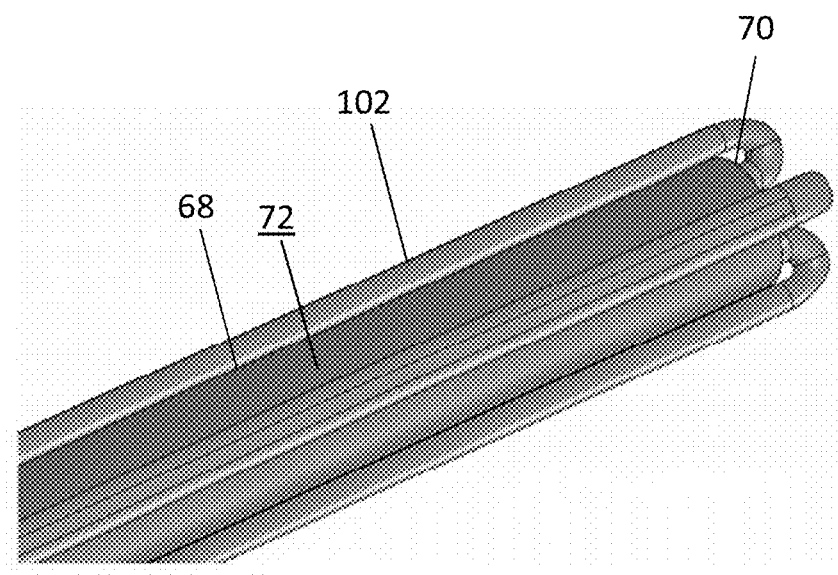
FIG. 10 is a dose-up back perspective view schematic representation of the proximal suture tube end of the suture tube, according to an embodiment.

Turning now to FIGS. 9 and 10, there are shown close-up perspective and close-up back perspective views schematic representations of a proximal suture tube end 70 of the suture tube 66, according to an embodiment. After the suture 102 extends into the distal suture tube end 68, it passes through the suture tube 66 to the proximal suture tube end 70, as shown in FIG. 9. The suture 102 extends out from the proximal suture tube end 70 is pulled back distally down an outer surface 72 of the suture tube 66, as shown in FIG. 10.

Referring now to FIG. 11, there is shown a perspective view schematic representation of the self-drilling anchor inserter 10, according to an embodiment. To create the self-drilling anchor inserter 10, the suture tube 66 (FIG. 6) is placed through and within a cannulated inserter tube 74. The inserter tube 74 has a proximal inserter end 76 and a distal inserter end 78. The distal inserter end 78 extends and connects to the proximal tip end 14 of the inserter tip 12.

Figure 12:
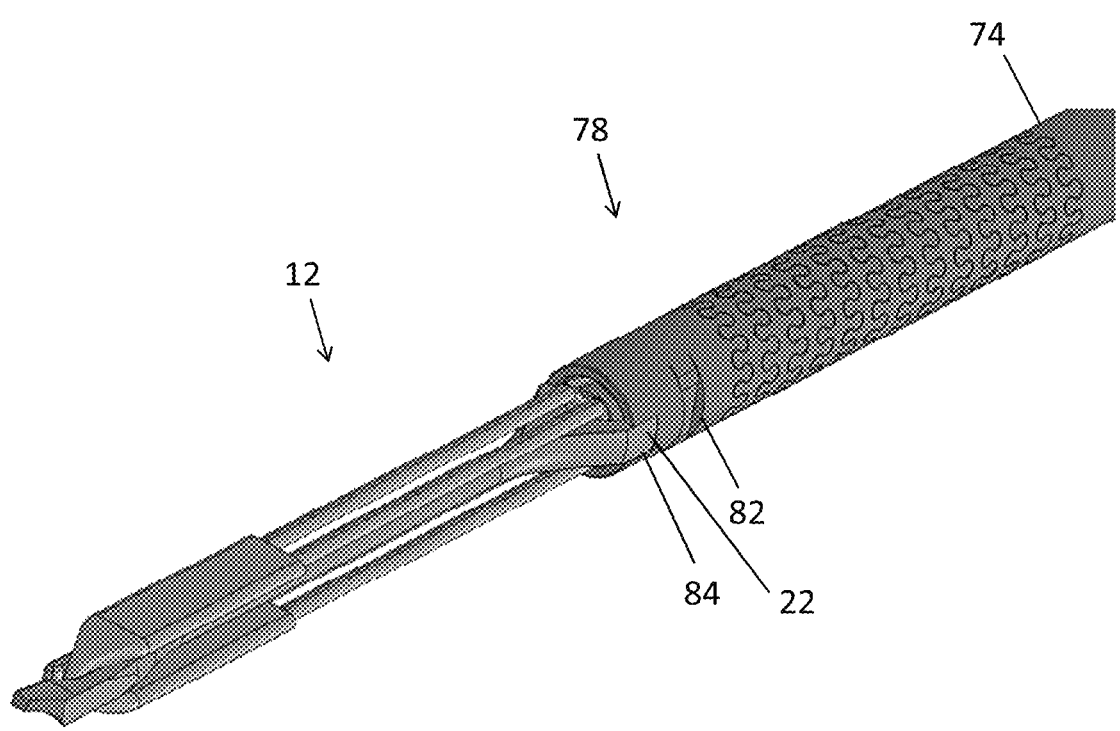
FIG. 12 is a close-up perspective view schematic representation of a distal inserter end of an inserter tube connected to the inserter tip, according to an embodiment.

Turning now to FIG. 12, there is shown a close-up perspective view schematic representation of a distal inserter end 78 of the inserter tube 74 connected to the inserter tip 12, according to an embodiment. The distal inserter end 78 comprises features for connecting the inserter tube 74 to the inserter tip 12. In particular, the distal inserter end 78 includes one or more interior protrusions 79 extending from an inner surface 81 of the inserter tube 74, as shown in FIG. 13. According to one embodiment, the interior protrusions 79 are created by crimping the distal inserter end 78. Thus, crimping the inserter tube 74 creates partially circumferential cavities 82 along an outer circumference of the inserter tube 74, while interior protrusions 79 are created along an inner circumference of the inserter tube 74. In the depicted embodiment, the distal inserter end 78 comprises two interior protrusions 79 spaced such that they are opposing.

Still referring to FIG. 12, the distal inserter end 78 additionally comprises one or more inserter slots 84 extending at least partially through the inserter tube 74. In the depicted embodiment, the inserter tube 74 comprises two inserter slots 84 spaced such that they are opposing. The inserter slots 84 of the inserter tube 74 are sized and configured to receive the protrusions 22 of the inserter tip 12. Likewise, the recesses 26 of the inserter tip 12 are sized and configured to receive the interior protrusions 79 of the inserter tube 74.

The resulting snap or press connection between the inserter tube 74 and the inserter tip 12 is shown in FIG. 13. In particular, FIG. 13 shows a partial transparent perspective view schematic representation of the distal inserter end 78 of the inserter tube 74 connected to the inserter tip 12, according to an embodiment. As shown, the connection between the inserter slots 84 of the inserter tube 74 and the protrusions 22 of the inserter tip 12 is a light press connection. The protrusions 22 fit into the inserter slots 84 to resist torsion and compressive loads. The interior protrusions 79 of the inserter tube 74 snap into the recesses 26 of the inserter tip 12 to interlock the inserter tube 74 and inserter tip 12 to resist tensile loads.

In the embodiment in FIG. 13, the distal inserter end 78 additionally includes fine laser cuts 86 extending along and into an outer surface 80 of the inserter tube 74. The fine laser cuts 86 allow the distal inserter end 78 to have some flexibility. As also shown in FIG. 13, when the suture tube 66 is locked within the inserter tube 74 via the connection of the inserter tube 74 to the inserter tip 12, the suture 102 extends in the annular space between the inserter tube 74 and the suture tube 66. In FIG. 13, free ends 112 of the suture 102 are shown extending distally along suture tube 66 between the suture tube 66 and the inserter tube 74.

Figure 14:
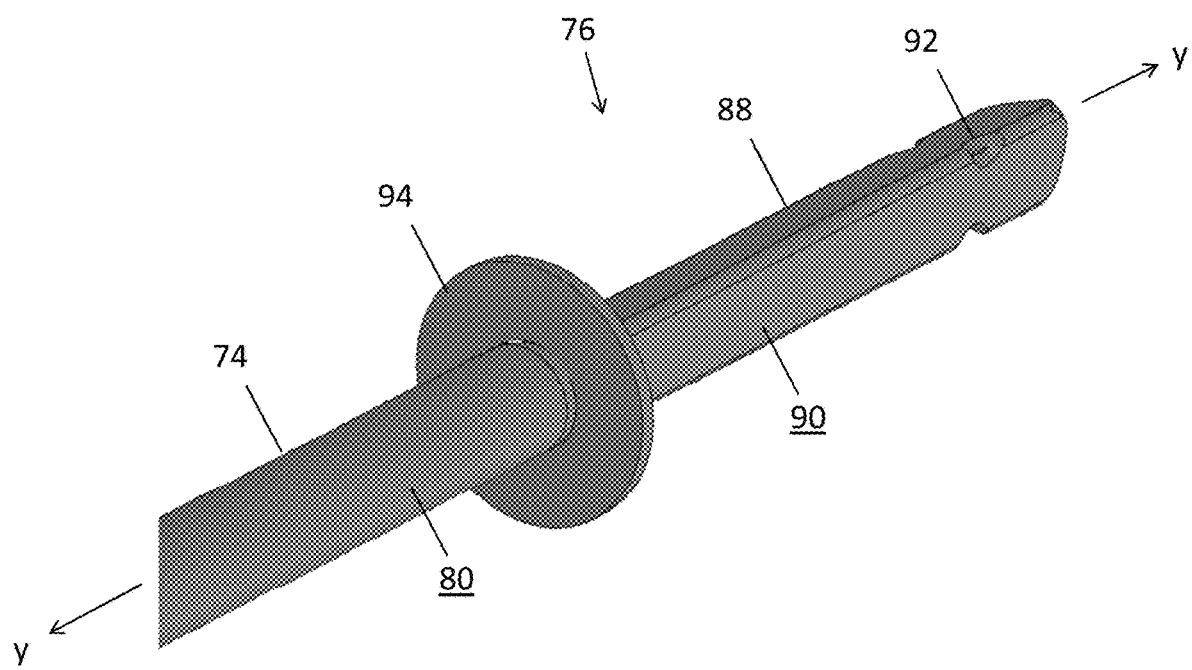
FIG. 14 is a close-up view schematic representation of a proximal inserter end of the inserter tube, according to an embodiment.

Referring now to FIG. 14 is a close-up view schematic representation of a proximal inserter end 76 of the inserter tube 74, according to an embodiment. The proximal inserter end 76 of the inserter tube 74 extends to a power handpiece interface, such as a quick change connector 88. A quick change connector 88 refers generally to a feature that facilitates the use of a power attachment for drilling. As shown in FIG. 11, the inserter tip 16 has a relatively thin profile compared to the inserter tube 74 and the quick change connector 88.

Referring back to FIG. 14, the quick change connector 88 is compatible with a traditional AO connection (as should be understood by a person of ordinary skill in the art in conjunction with a review of this disclosure). However, other connections, such as a Trinkle or Hudson connection can be used. In the depicted embodiment, the quick change connector 88 comprises one or more flat surfaces 90 extending along an axis parallel to the central longitudinal y-y axis. In particular, the quick change connector 88 comprises three flat surfaces 90, having a triangular cross-section. The quick change connector 88 also comprises three grooves 92, which extend into the quick change connector 88 at positions wherein the two of the three flat surfaces 90 meet or otherwise converge. However, the three flat surfaces 90 permit the central longitudinal y-y axis of the self-drilling anchor inserter 10 to be co-linear with a central longitudinal y-y axis extending through a grasping chuck (not shown).

The quick change connector 88 can be formed from a solid piece of metal or formed into the proximal inserter end 76 of the inserter tube 74 (shown in FIG. 14). Forming the quick change connector 88 into tubing offers many advantages for use with the self-drilling anchor inserter 10. For example, the proximal inserter end 76 is kept open to allow better flow of Ethylene Oxide for sterilization of the suture material housed inside the tubing and there can be a reduction in the number of components needed for assembly of the self-drilling anchor inserter 10.

Figure 22:
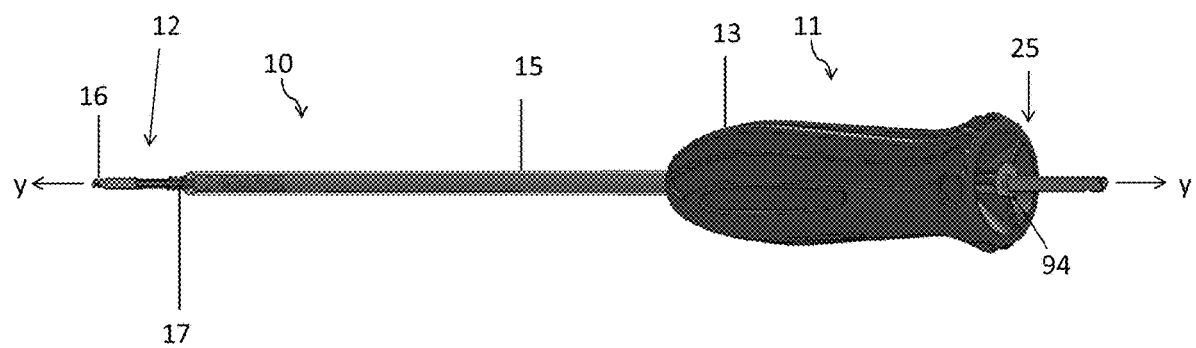
FIG. 22 is a side perspective view schematic representation of the self-drilling anchor inserter in an extracted position, according to an embodiment.

Still referring to FIG. 14, the proximal inserter end 76 of the inserter tube 74 comprises a hard stop feature 94. As shown in the depicted embodiment, a hard stop feature 94 is positioned or otherwise located along the proximal inserter end 76 of the inserter tube 74. The hard stop feature 94 is distal relative to the quick change connector 88 such that the hard stop feature 94 prevents the quick change connector 88 from entering or advancing through a guide 11 (FIG. 22). In the depicted embodiment, the hard stop feature 94 is a ring wrapped around the outer surface 80 of the inserter tube 74. However, any other shape or configuration for a hard stop feature 94 can be used if sufficiently sized larger than a diameter of the guide 11.

Figure 15:
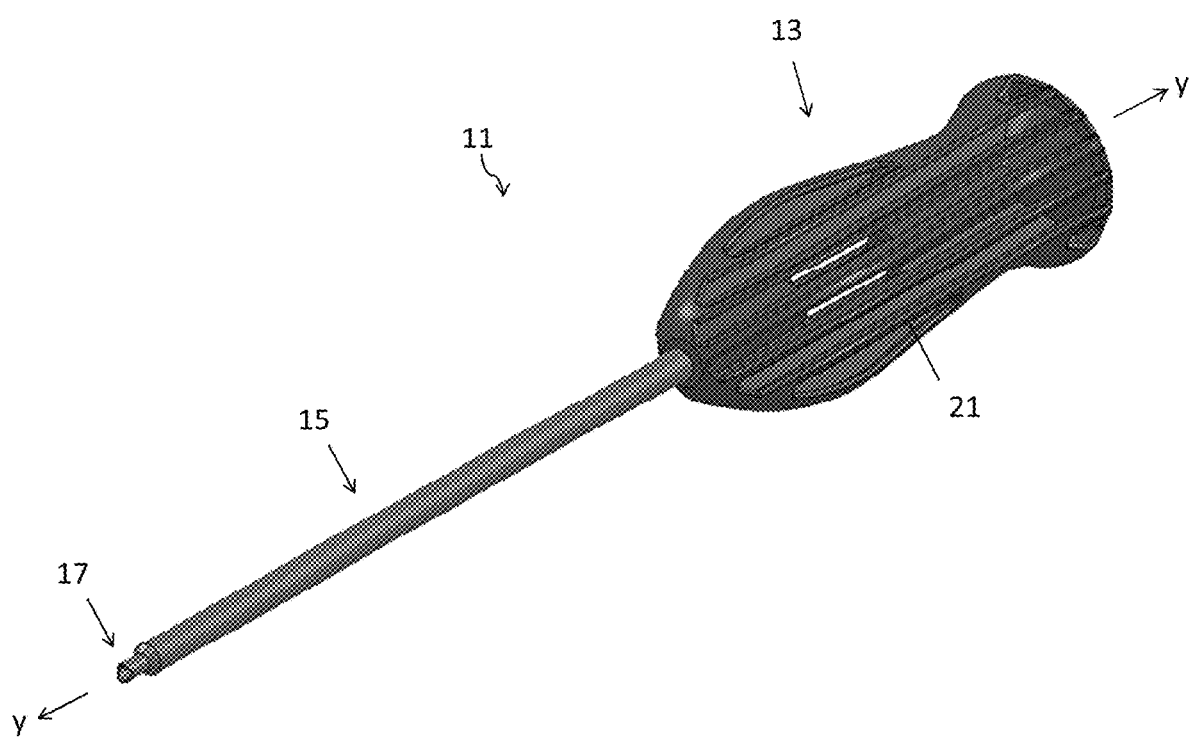
FIG. 15 is a perspective view schematic representation of a guide, according to an embodiment.
Figure 16:
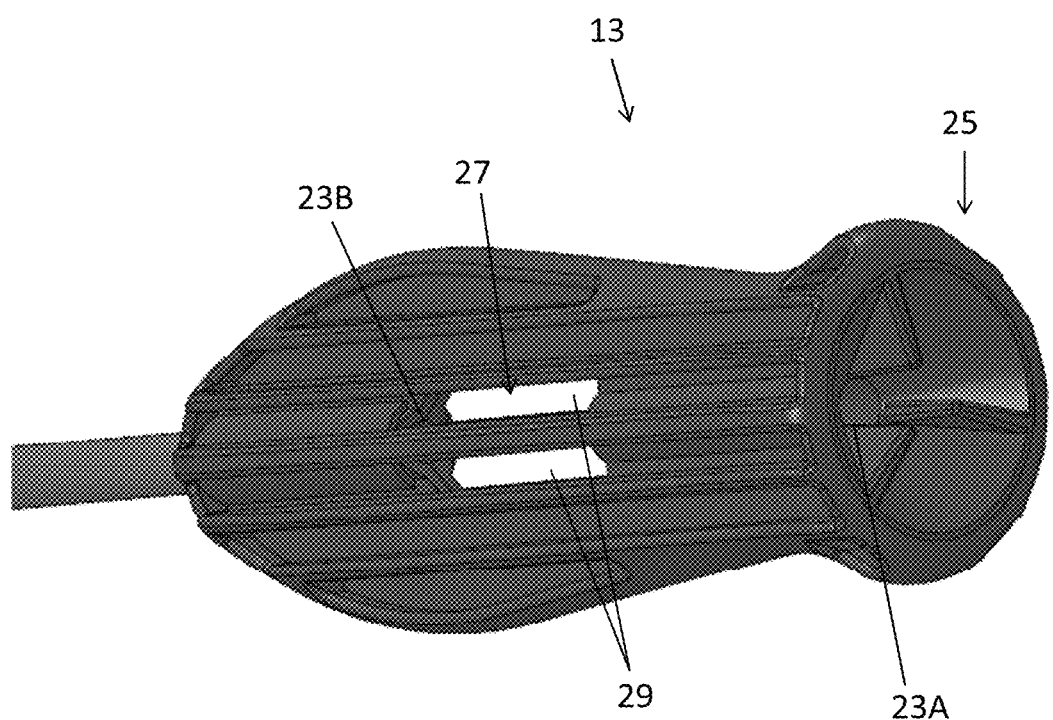
FIG. 16 is a back perspective view schematic representation of the guide, according to an embodiment.

Turning now to FIGS. 15 and 16, there are shown perspective and back perspective views schematic representations of the guide 11, according to an embodiment. The guide 11 comprises a proximal guide handle 13 connected to a cannulated guide tube 15 with a central longitudinal y-y axis extending therethrough. The guide tube 15 extends distally from the guide handle 13 to a guide tip 17, as shown in FIG. 15. The guide handle 13 may be ergonomically shaped with exterior ridges 21 for an improved grip. As shown in FIG. 16, the guide handle 13 is cannulated such that a handle channel extending through the guide handle 13 aligns with a tube channel extending through the guide tube 15.

In the embodiment shown in FIGS. 15-16, the handle channel is comprised of first and second channel portions 23A, 23B. The first channel portion 23A extends to a proximal handle end 25 of the guide handle 13, while the second channel portion 23B connects to the guide tube 15. The first and second channel portions 23A, 23B are separated by a space 27 within the guide handle 13. In addition, one or more openings 29 extend through the guide handle 13 and into the space 27, as shown in FIG. 16. The space 27 and openings 29 allow fluid to escape the guide 11 rather than flow out of the proximal handle end 25.

Figure 17:
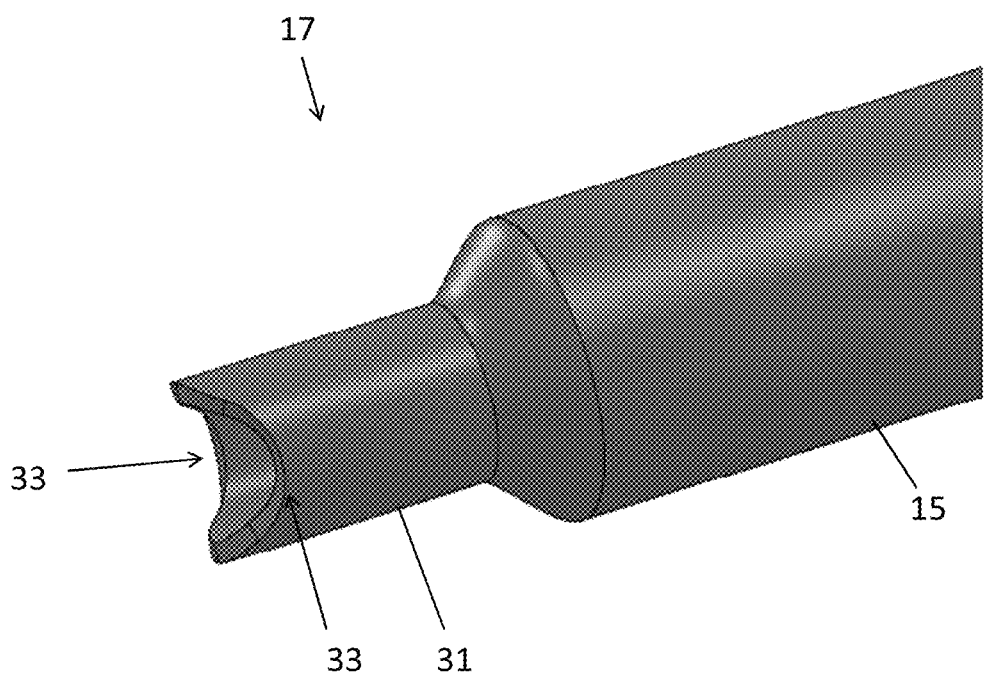
FIG. 17 is a close-up perspective view schematic representation of a guide tip, according to an embodiment.
Figure 18:
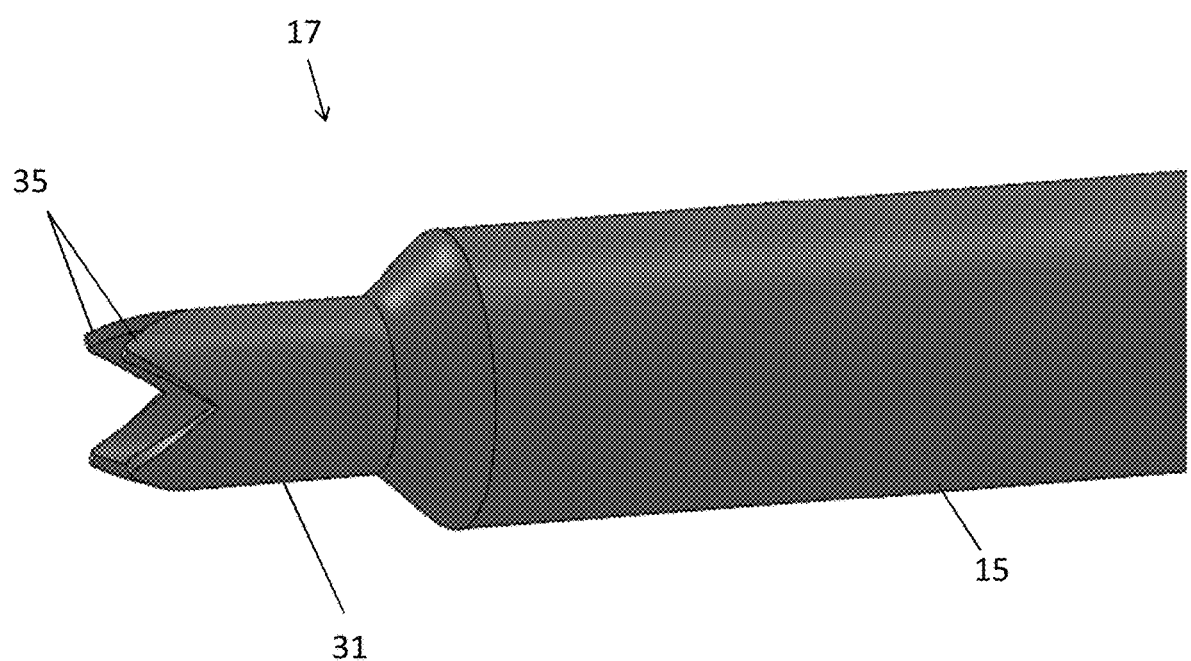
FIG. 18 is a close-up perspective view schematic representation of a guide tip, according to an alternative embodiment.
Figure 19:
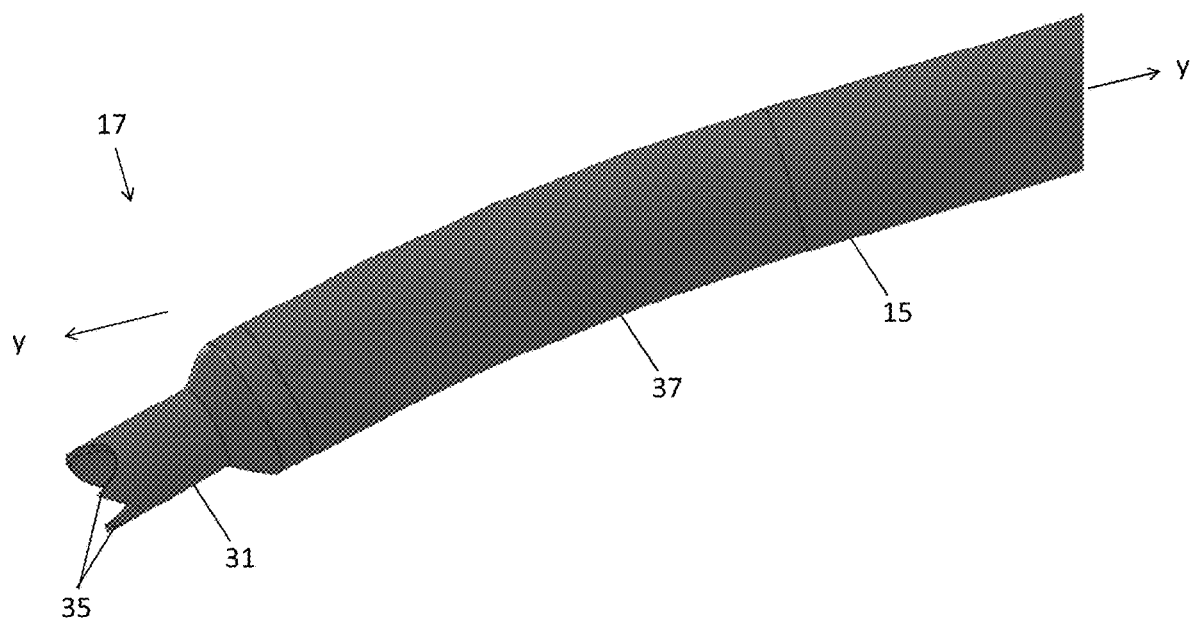
FIG. 19 is a close-up perspective view schematic representation of a guide tip, according to another embodiment.

Referring now to FIGS. 17-19, there are shown close-up perspective views schematic representations of the guide tip 17, according to multiple embodiments. In the embodiment shown in FIGS. 15 and 17, the guide tip 17 has a fish mouth shape. Specifically, the guide tip 17 is guide tip tube 31 with two reduced diameter areas 33. In other words, the length of the guide tip tube 31 is shorter in two areas 33. These areas 33 are half-moon shaped, creating the fish mouth shape of the guide tip 17. The fish mouth shape of the guide tip 17 allows it to compress the anchor 100 and provide stability during insertion.

In the embodiment shown in FIG. 18, the guide tip 17 has a crown shape. Specifically, the guide tip 17 has protrusions 35 extending distally therefrom. In the depicted embodiment, the protrusions 35 are triangular and extend distally from the guide tip tube 31. In the embodiment shown in FIG. 19, the guide tip 17 is crown-shaped, but the guide tube 15 comprises a distal curved portion 37. The distal curved portion 37 is curved away from the central longitudinal y-y axis extending through the guide 11.

Figure 20:
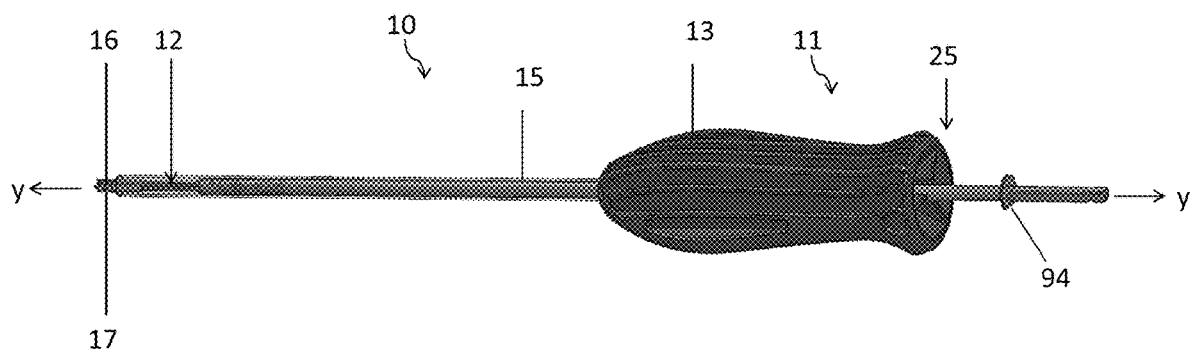
FIG. 20 is a side perspective view schematic representation of the self-drilling anchor inserter in a retracted position, according to an embodiment.
Figure 21A:
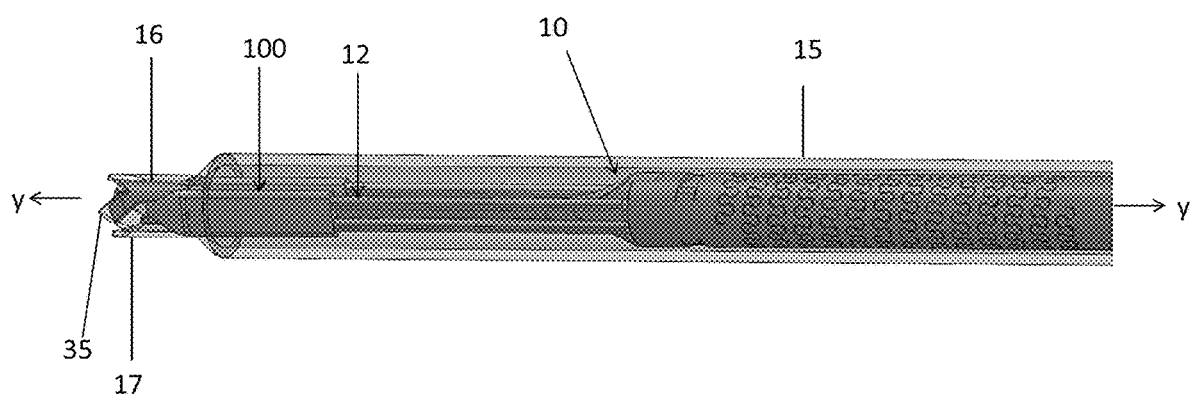
FIG. 21A is a side perspective view schematic representation of the distal tip end of the self-drilling anchor inserter in the retracted position, according to an embodiment.
Figure 21B:
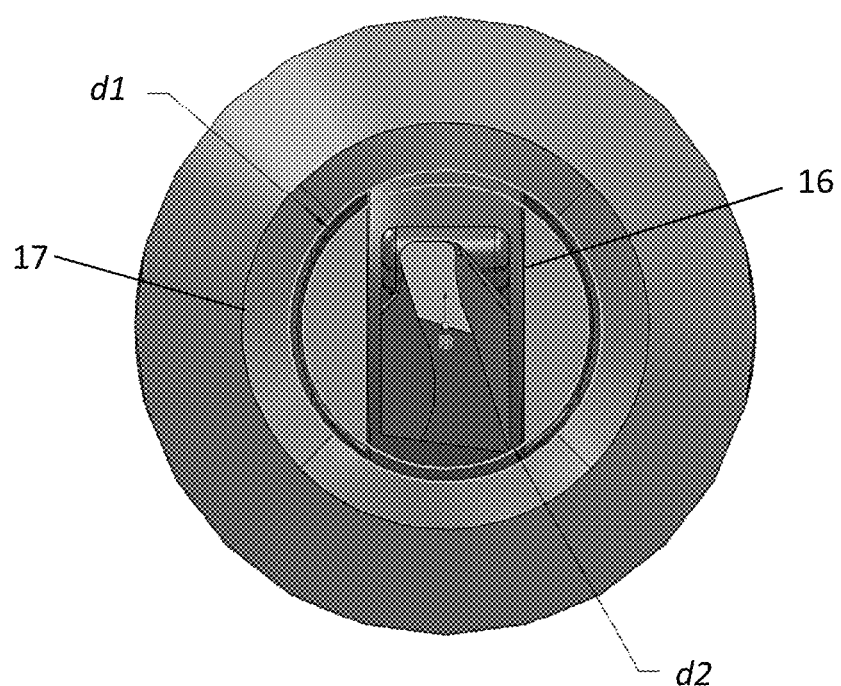
FIG. 21B is a close-up front view schematic representation of the distal tip end of the inserter tip within the guide tip, according to an embodiment

Turning now to FIG. 20, there is shown a side perspective view schematic representation of the self-drilling anchor inserter 10 in a retracted position, according to an embodiment. In use, the self-drilling anchor inserter 10 is placed through the guide 11 (via the cannulated guide handle 13 and cannulated guide tube 15). In the retracted position, the distal tip end 16 of the inserter tip 12 is within the guide tip 17, as shown in FIG. 20. As shown in the embodiment in FIG. 21A, the distal tip end 16 is within the crown-shaped guide tip 17. The protrusions 35 of the guide tip 17 extend distally past the distal tip end 16. In the retracted position, the anchor 100 is maintained within the guide tube 15 prior to insertion. As also shown in FIG. 21B, the guide tip 17 has a diameter d1 that is approximately the same as (or slightly larger than) a diameter d2 of the distal tip end 16. The similar diameters d1, d2 are designed for minimal clearance between them.

Figure 23:
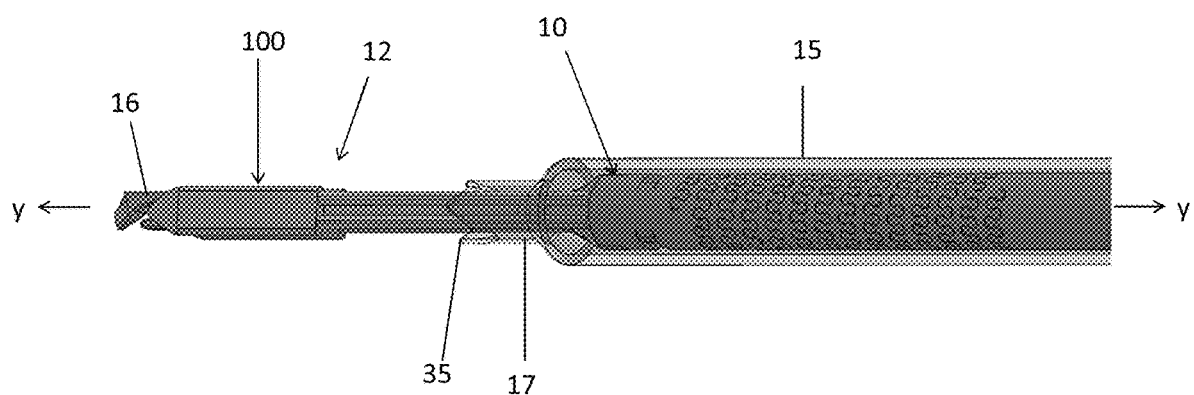
FIG. 23 is a side perspective view schematic representation of the distal end of the self-drilling anchor inserter in the extracted position, according to an embodiment.

Referring now to FIG. 22, there is shown a side perspective view schematic representation of the self-drilling anchor inserter 10 in an extracted position, according to an embodiment. To move the self-drilling anchor inserter 10 from the retracted position to the extended position, the self-drilling anchor inserter 10 is extended through the guide 11 in the distal direction. The self-drilling anchor inserter 10 can be extended through the guide 11 until its hard stop feature 94 contacts a proximal handle end 25 of the guide 11. As shown in the embodiment in FIG. 23, the distal tip end 16 extends past the crown-shaped guide tip 17 in the distal direction. The distal tip end 16 extends distally past the protrusions 35 of the guide tip 17. When the self-drilling anchor inserter 10 is in the extended position, the anchor 100 is inserted and can be deployed.

Figure 24A:
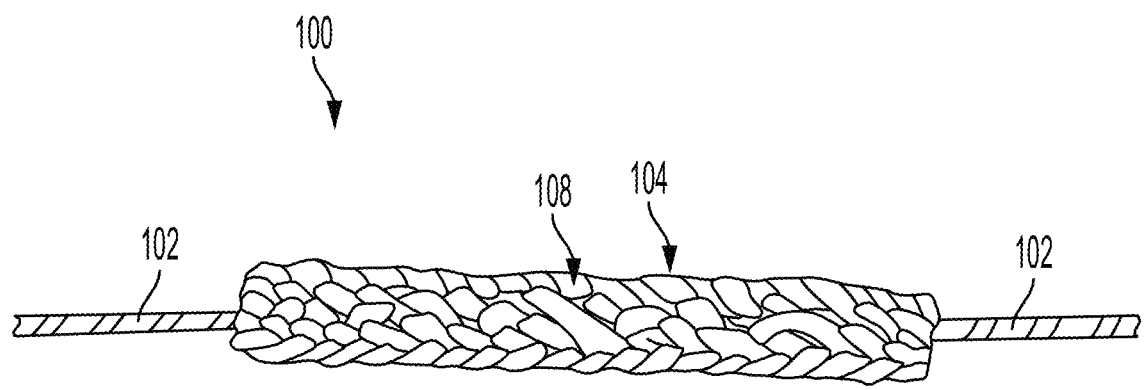
FIG. 24A is a back view schematic representation of an all-suture anchor, according to an embodiment.
Figure 24B:
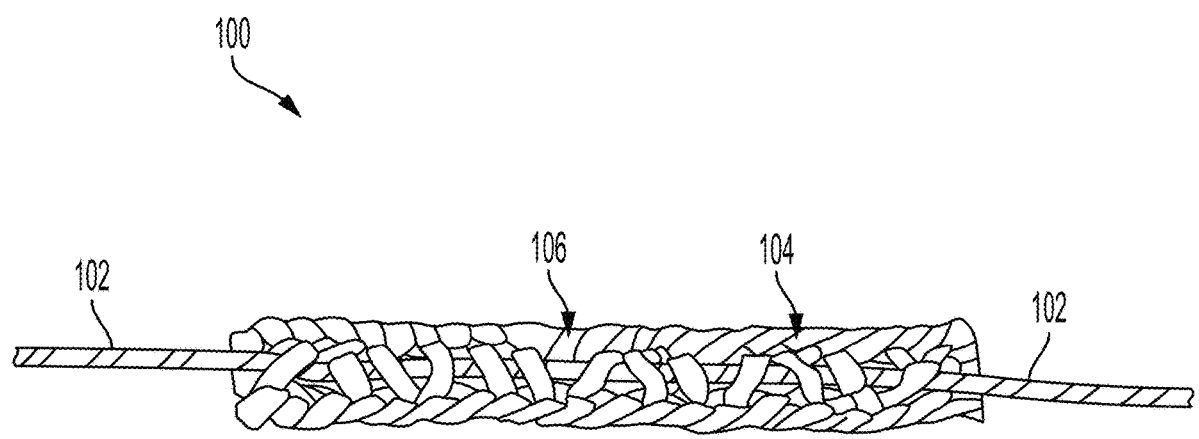
FIG. 24B is a top view schematic representation of the all-suture anchor of FIG. 24A.
Figure 25A:
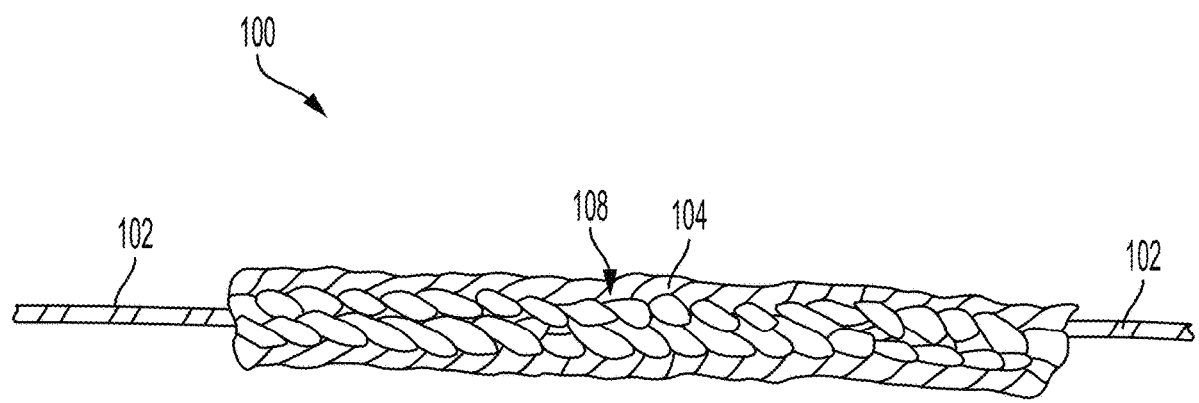
FIG. 25A is a back view schematic representation of an all-suture anchor, according to an embodiment.
Figure 25B:
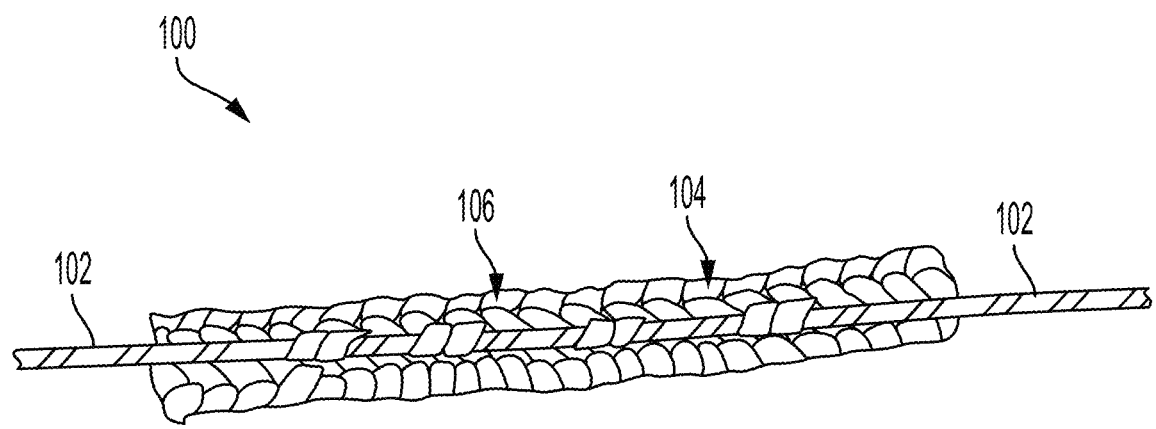
FIG. 25B is a top view schematic representation of the all-suture anchor of FIG. 25A.

Referring briefly to FIGS. 24A-24B, there are shown front and back views schematic representations of the all-suture anchor 100, according to an embodiment. FIG. 24A shows a back view of an all-suture anchor 100, while FIG. 24B shows the front view. As shown, the length of suture 102 passing into and out of the anchor braid/fibrous construct 104 only passes through one (e.g., "front") surface 106 of the anchor braid 104 (FIG. 24B). Similarly, FIGS. 25A-25B also show a back view (FIG. 25B) and front view (FIG. 25A) where the suture 102 passing only through one (e.g., "front") surface 106 of the anchor braid 104 (FIG. 25B). When the all-suture anchor 100 has suture 102 passing only through one (e.g., "front") surface 106, the anchor braid 104 protects the suture 102 from abrasion on the opposing (e.g., "back") surface 108 (FIGS. 24A and 25A) when loaded onto the inserter (as should be understood by a person of ordinary skill in the art in conjunction with a review of this disclosure). In FIGS. 24A-25B, the suture 102 is passed through the anchor braid 104 at numerous passing locations. The number of passing locations in FIGS. 26B and 27B is eight passing locations 110, while the number of passing locations for some alternative all-suture anchors 100 is six passing locations 110. The number of passing locations 110 can vary depending on the composition and size of the suture 102 and/or anchor braid 104. The number of passing locations 110 can be optimized by balancing input parameters, such as anchor braid length, anchor braid width, anchor braid pick density, suture diameter, and others, to yield output parameters, such as manufacturability, anchor creep under load, and pullout strength.

Figure 28A:
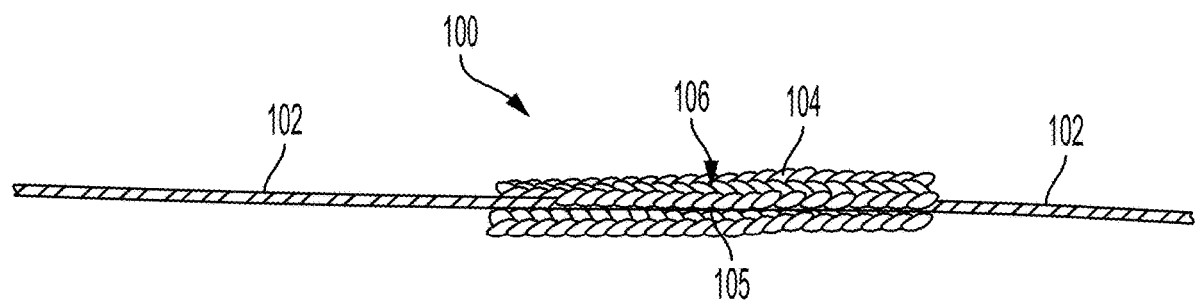
FIG. 28A is a top view schematic representation of an all-suture anchor, according to an embodiment.
Figure 28B:
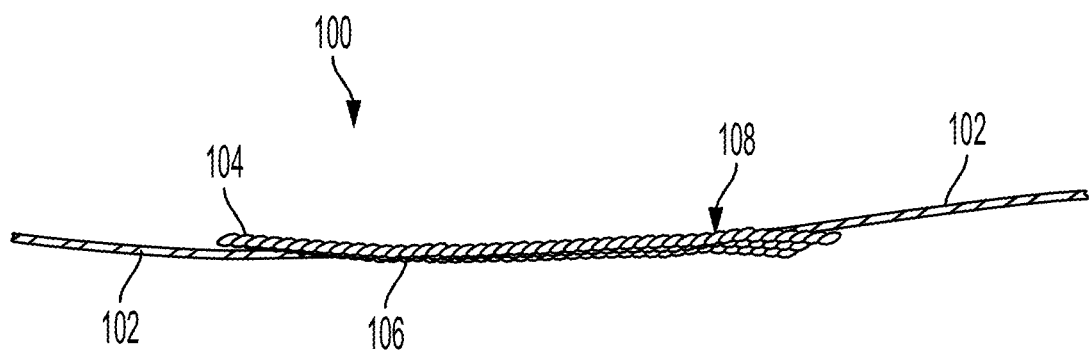
FIG. 28B is a side view schematic representation of the all-suture anchor in FIG. 28A.

Turning briefly to FIGS. 28A-28B, there are shown top and side views schematic representations of an all-suture anchor 100, according to an alternative embodiment. As shown in FIGS. 28A-28B, the length of suture 102 passes through an approximate center 105 of the anchor braid 104. In the depicted embodiment, the length of suture 102 enters the anchor braid 104 through one (e.g., "front") surface 106 and exits through the opposing (e.g., "back") surface 108 of the anchor braid 104. With the length of suture 102 positioned on both sides of the anchor braid 104, the anchor braid 104 can be loaded onto the inserter 10 such that anchor braid 104 can be positioned against a bone, while the lengths of suture 102 are along the inserter 10, as shown in FIGS. 11-13.

Figure 29A:
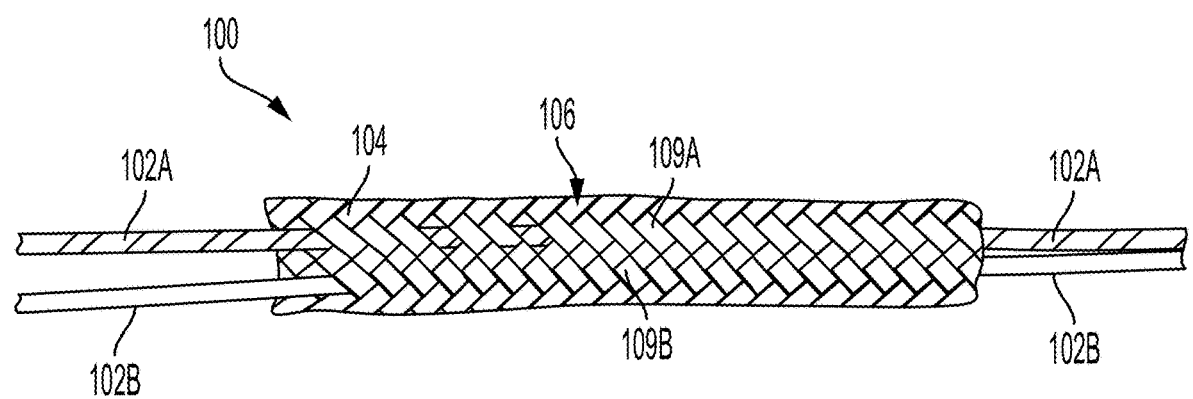
FIG. 29A is a top view schematic representation of an anchor braid loaded with two lengths of suture, according to an embodiment.
Figure 29B:
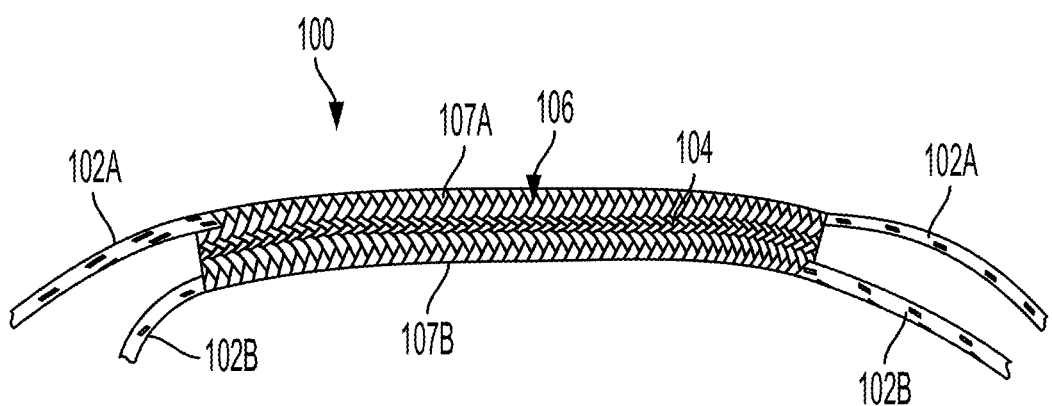
FIG. 29B is a top view schematic representation of an anchor braid loaded with two lengths of suture, according to an alternative embodiment.

In another alternative embodiment, as shown in FIGS. 29A-29B, the anchor braid 104 can be loaded with multiple lengths of suture 102A, 102B. In the depicted embodiment, the anchor braid 104 is loaded with two lengths of suture 102A, 102B. The lengths of suture 102 may extend through the anchor braid 104 along its opposing edges 107A, 107B (FIG. 29B), through two off-center locations 109A, 109B (FIG. 29A), or any conceivable combination thereof (including an extension of the length of suture 102A, 102B through the approximate center 105 of the anchor braid 104). In addition, the lengths of suture 102A, 102B may enter/exit the anchor braid 104 on the same surface (FIGS. 24A-25B) or on opposing surfaces (FIGS. 28A-28B).

Figure 30A:
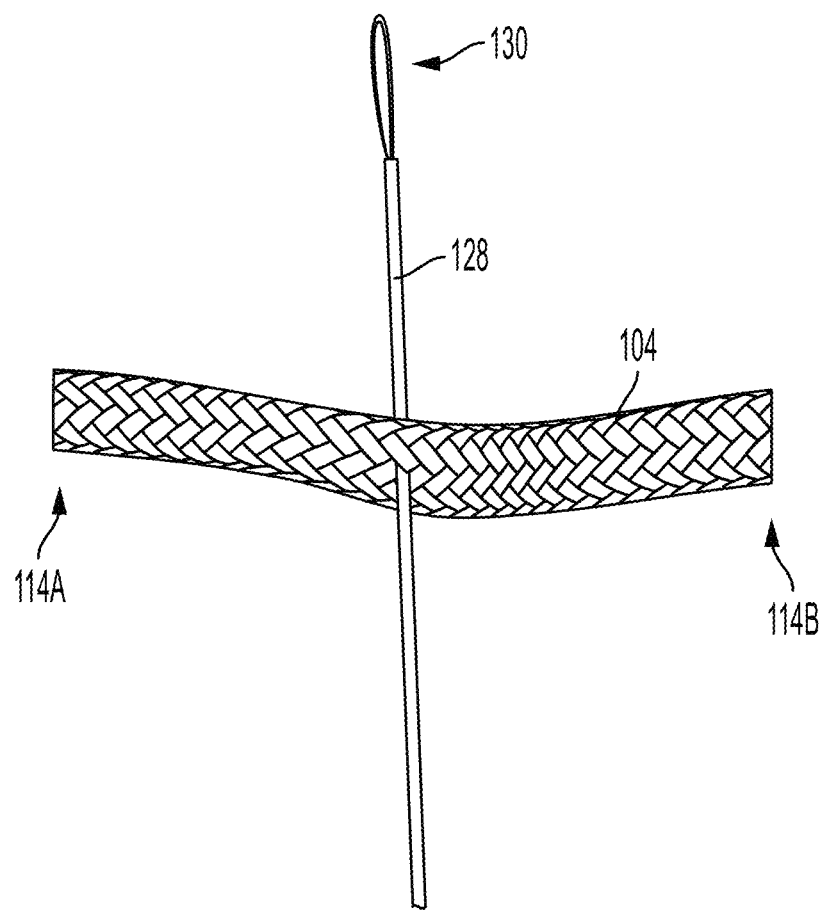
FIG. 30A is a top view schematic representation of a threader passed through an anchor braid, according to an embodiment.
Figure 30B:
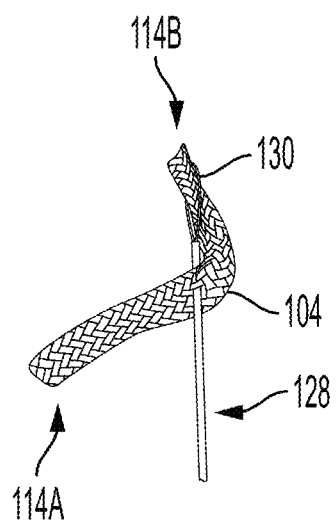
FIG. 30B is a top view schematic representation of the anchor braid of FIG. 30A with a first end loaded into the threader.
Figure 30C:
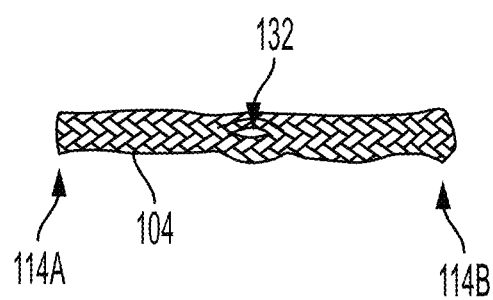
FIG. 30C is a top view schematic representation of the anchor braid of FIG. 30A with a central eyelet.
Figure 31:
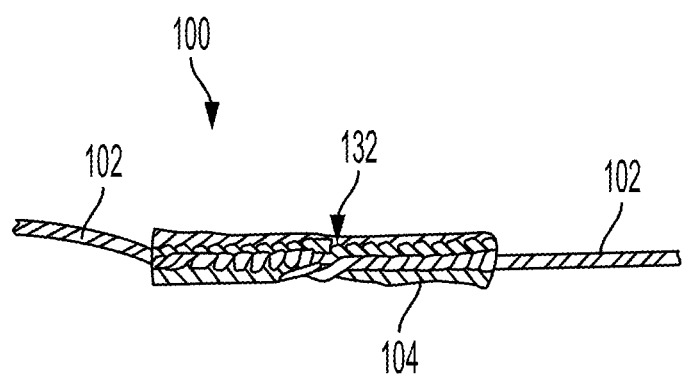
FIG. 31 is a top view schematic representation of the anchor braid of FIG. 30C with a length of suture passing through the central eyelet.

Referring now to FIGS. 30A-31, there are shown top views schematic representations of an all-suture anchor 100, according an additional alternative embodiment. FIGS. 30A-30C depict the process for creating an inverted anchor braid 104. As shown in FIG. 30A, a threader 128 with a threader loop 130 is first passed through the anchor braid 104. Then, in FIG. 30B, an end 114B of the anchor braid 104 is pulled through the threader loop 130. Finally, the threader loop 130 is pulled back through the anchor braid 104, creating a central eyelet 132, as shown in FIG. 30C. A length of suture 102 can be loaded onto the inverted anchor braid 104 by passing the length of suture 102 through the anchor braid 104, as described in conjunction with any of the embodiments shown in FIGS. 24A-25B, 28A-28B, and FIGS. 29A-29B, and passing through the central eyelet 132, as shown in FIG. 31.

Figure 26A:
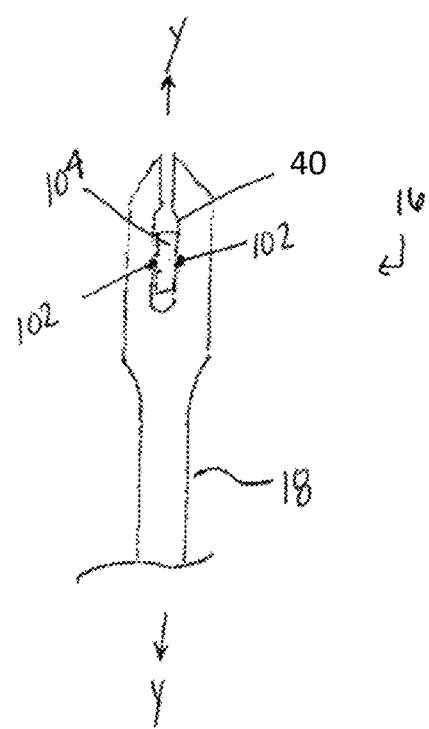
FIG. 26A is a top view schematic representation of an all-suture anchor loaded onto the inserter tip, according to an embodiment.
Figure 26B:
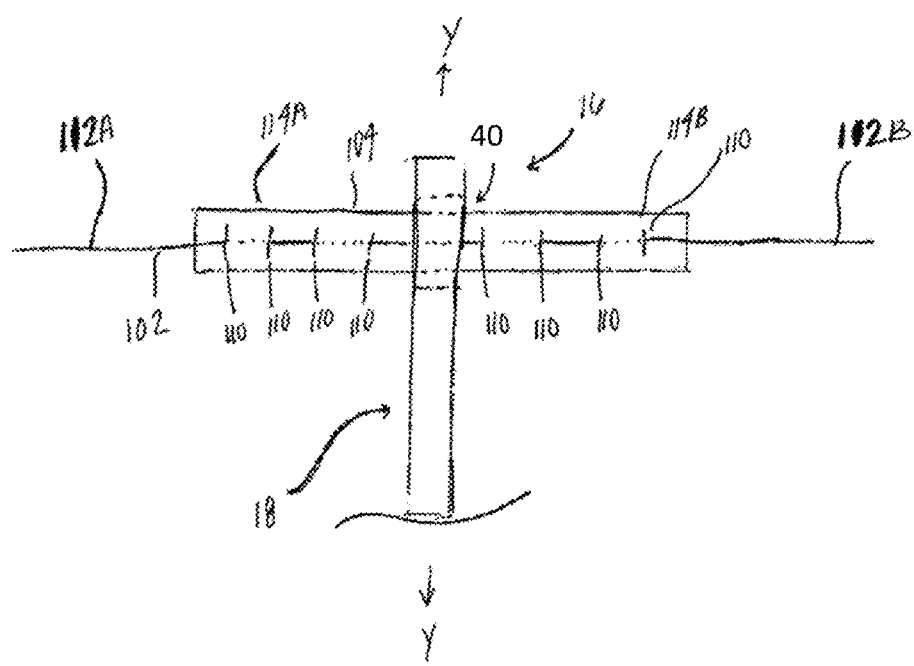
FIG. 26B is a side view schematic representation of the all-suture anchor loaded onto the inserter tip of FIG. 26A.

Referring back to FIGS. 24A-25B, from the unloaded, pre-deployment configuration shown, the all-suture anchor 100 is loaded onto the inserter tip 16, as shown in the exemplary embodiment of the inserter tip 16 in FIGS. 26A-26B. To load the inserter tip 16, the anchor braid 104 is fed through the suture anchor retention slot 40 such that a pair of ends 112A, 112B of the suture 102 and a pair of ends 114A, 114B of the anchor braid 104 are on opposing sides of the suture anchor retention slot 40 (and inserter 10). Further, in one embodiment, the all-suture anchor 100 is fed through the suture anchor retention slot 50 such that four of the passing locations 110 are on opposing sides of the suture anchor retention slot 40 (and inserter 10). The suture 102 is then pulled taut along the shaft 18 of the inserter tip 16, which causes the pair of ends 112A, 112B of the suture 102 and the pair of ends 114A, 114B of the anchor braid 104 to extend along the inserter 10 (i.e., each along an axis approximately parallel to the central longitudinal y-y axis).

Figure 27A:
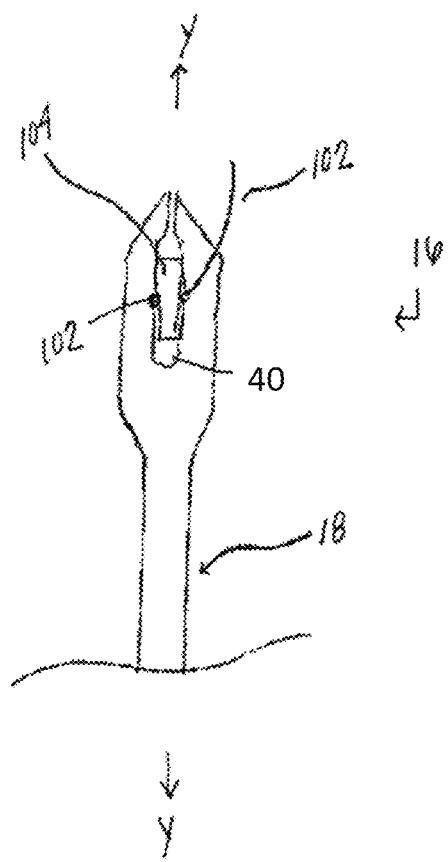
FIG. 27A is a top view schematic representation of an all-suture anchor loaded onto the inserter tip, according to an alternative embodiment.
Figure 27B:
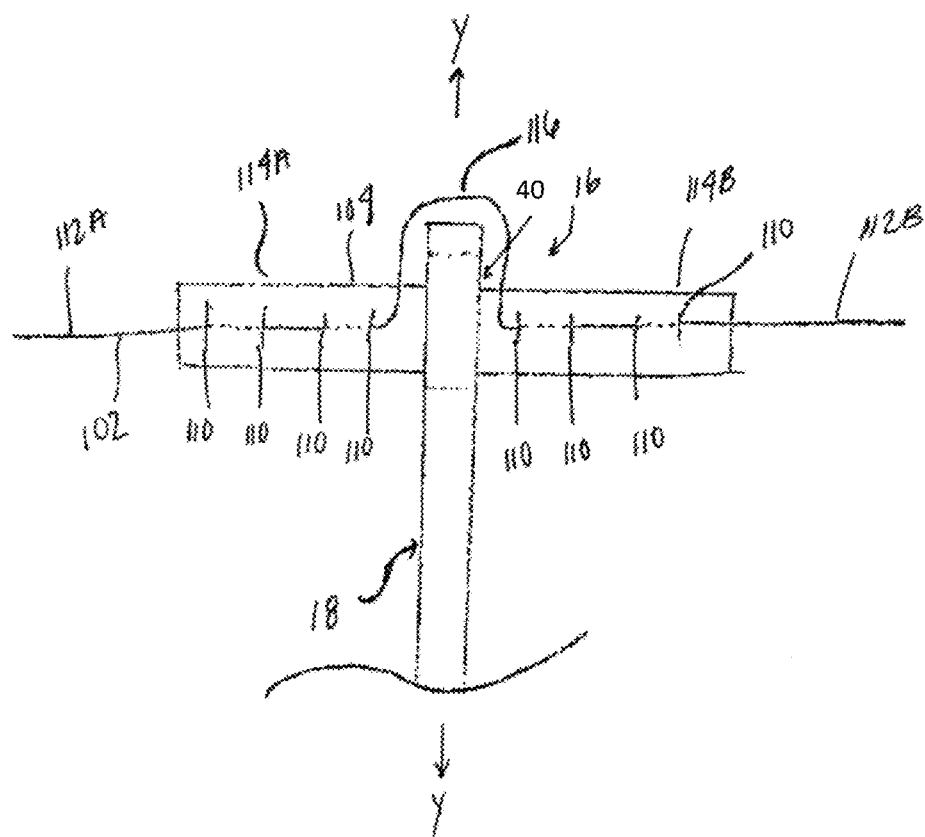
FIG. 27B is a side view schematic representation of the all-suture anchor loaded onto the inserter tip of FIG. 27A.

Turning now to FIGS. 27A-27B, there are shown top views schematic representations of an all-suture anchor, according to an alternative embodiment, in the unloaded, pre-deployment configuration and the loaded, pre-deployment configuration. The all-suture anchor 100 shown in FIGS. 27A-27B is a Y-Knot suture anchor. Certain structural and functional aspects of embodiments of the present invention are similar to embodiments of the soft suture anchor described and illustrated in U.S. Pat. No. 9,826,971. Those similarities should be understood by a person of ordinary skill in the art in conjunction with a review of this disclosure and accompanying drawings in conjunction with the published application, and are not further discussed in detail herein. Certain differences, including various inventive features of embodiments of the present invention are further briefly described herein and below with reference to the accompanying drawings. However, in the embodiment wherein the all-suture anchor 100 is a Y-Knot suture anchor, only the anchor braid 104 is loaded into the inserter tip 16. As shown in FIG. 27B, when the anchor braid 104 is loaded in the suture anchor retention slot 40, a central portion 116 of the suture 102 is pulled away from (i.e., in a direction distal to) the inserter tip 16. This prevents the suture 102 from falling into the suture anchor retention slot 40. Keeping the suture 102 out of the suture anchor retention slot 40 avoids potential damage to the suture 102 due to heat generated in the arms 28, 32 (FIGS. 2-3) of the inserter 10 as it is drilled into bone or from being severed upon removal of the inserter 10.

Turning now to FIGS. 32A-32B, there are shown top views schematic representations of an anchor braid 104 with an additional material 120, according to an embodiment. One of ordinary skill in the art should recognize and appreciate potential embodiments of a Y-Knot anchor with additional material, such as monofilament polymers, to add strength. Additional material can be applied to the all-suture anchor 104. As shown in FIG. 32A, the anchor braid 104 is folded in half. A monofilament 120 is used to stitch together each (i.e., two) side edge 122A, 122B of the anchor braid 104 to create an enclosed area 124 with the length of suture 102 inside, as shown in FIG. 32B. In addition to improved strength, this will prevent the anchor braid 104 from rolling over on itself during insertion and exposing the suture 102 to the bone, causing abrasion. Additionally, the described twisting of the anchor braid 104, in combination with a more dense material running in the axis of the anchor braid 104 can result in a threaded all-suture anchor 100.

Referring now to FIG. 33, there is shown a side view schematic representation of the inserter 10 in the loaded, pre-deployment configuration at a bone hole location 39, according to an embodiment. As shown, the inserter 10 is extended through a guide 11 at a selected bone hole location 39 such that the guide tip 17 is positioned at the surface 41 of the bone 43. In the depicted embodiment, the inserter tip 16 loaded with the anchor braid 104 in the guide tip 17 is positioned at the surface 41 of the bone 43. Once positioned and while the guide 11 is held stationary relative to the bone 43, the user rotates the inserter via the quick change connector 88 using a handpiece, which rotates the inserter tip 16, and pushes the inserter 10 into the bone 43 until the anchor braid 104 is fully inserted into the bone 43. Features, such as the hard stop feature 94 (FIG. 14) limit the insertion depth by not allowing the inserter 10 to go further through the guide 11.

Turning now to FIG. 34, there is shown a side view schematic representation of the inserter 10 in the loaded, pre-deployment configuration in a bone hole 45, according to an embodiment. As shown, the inserter tip 16 forms a hole 45 in the bone 43 as the inserter 10 advances in the guide 11. Once the anchor braid 104 is inserted into the bone hole 45, the inserter 10 is removed leaving the anchor braid 104 behind in the bone hole 45. The force to keep the anchor braid 104 in the bone hole 45 may be provided by interaction between the bone 43 and the anchor braid 104 or by interaction between the anchor braid 104 and another member introduced to hold the anchor braid 104 in place before the all-suture anchor 100 is deployed.

Referring now to FIG. 35, there is shown a side view schematic representation of the inserter 10 in the unloaded, post-deployment configuration, according to an embodiment. Once the anchor braid 104 is fully inserted and the inserter 10 is removed, tension is applied to the suture 102 (ends 112A, 112B) by removal of the inserter 10, the user pulling directly on the suture 102 (ends 112A, 112B) or a combination of both means. The tension causes the anchor braid 104 to deploy into a post-deployment configuration to provide fixation.

Turning now to FIGS. 36A-36B, there are shown side view schematic representations of an embodiment of the all-suture anchor 100 in the pre-deployment and post-deployment configurations. In the depicted embodiment, the all-suture anchor 100 is a soft suture anchor, such as the Y-Knot® anchor 200. One such suture anchor is disclosed in U.S. Pat. No. 9,826,971 assigned to the assignee hereof and incorporated by reference herein in its entirety.

An embodiment of the Y-Knot® anchor (or soft anchor or "all-suture" anchor) 200 is illustrated in detail in FIGS. 36A-36B. The Y-Knot® anchor 200, as shown in FIGS. 36A-36B, contains at least two sections: at least one suture 202, which is a suture to be anchored; and an anchor body 204, which is to form a portion of the anchor 200 that can increase in width, thickness and/or diameter and shrink in length as part of deployment. See FIG. 36A, showing the anchor body 204 in the pre-deployment configuration; and FIG. 36B, showing the anchor body 204 "shortened" and "expanded" in the post-deployment configuration, which is additive to the increase due to the pleats. This soft anchor embodiment also takes advantage of Poisson's ratio, which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. Although, it is the anchor body 204 that increases in width, thickness and/or diameter at deployment, it should be understood that the suture 202 can also play a role in the deployment of the anchor 200 even though the suture 202 may remain free (in some embodiments) to slide, and non-slidable in others (at least at a particular position or point in use) in relation to the anchor body 204. The suture 202 helps to position, align and support the anchor body 204, such that if the suture 202 were to be removed from the anchor body 204 after deployment of the anchor 200, the anchor body 204 may be free to spill (i.e., release), allowing the anchor body 204 to collapse and shrink in size, allowing for easy (and potentially undesirable) removal.

In other words, the anchor body 204 has two primary functions. First, it becomes a base for the suture 202 to slide within. Second, when compressed and/or pleated during deployment, the anchor body 204 becomes more compact in one direction thereby expanding outwardly and increasing its overall width, thickness or diameter to create a retention capacity. This action of having the anchor body 204 change in shape to increase its overall width, thickness or diameter is a useful characteristic which may be used advantageously to secure the anchor 200 in a hole 45 or against a bony or soft tissue 43. It is this combination of the expanding anchor body 204 coupled with the suture 202 remaining slidable (in some embodiments; and non-slidable in others, at least at a particular position or point in use) in relation to the anchor body 204 that render embodiments of the present invention ideal for the reattachment of soft tissue to bone 43 or soft tissue to soft tissue where it is desirable to pass sliding knots to secure a repair.

The discussion below relates to alternative embodiments of a disposable handpiece, alternative embodiments of all-suture anchors that can be used in conjunction with/deployed by embodiments of the anchor inserter described herein, and an alternative embodiment of an anchor installation device/inserter and drill.

Turning to FIG. 37, a side view schematic representation of a disposable handpiece 300 according to an alternative embodiment is shown. The disposable handpiece can include, but is not limited to, a motor 301, a chuck 302, disposable battery(ies) 303 configured to supply power to the motor, and at least one switch 304 configured to be actuated (rotationally, linearly, perpendicular to the longitudinal axis of the device ("pushed")) by a user to turn on the drill bit 302, and/or set the desired speed of the drill bit 302. Alternatively, the motor can be actuated by a predetermined force (enough to start drilling a hole in a particular bone, which could change depending on type and hardness of a bone) imparted by a user via the handpiece 300 on to the inserter against bone. The handpiece 300 can also include a disposable plastic housing 305 to make the device lightweight, less expensive, and disposable. The disposable plastic housing 305 can be made from any plastic or combination of plastics. The inserter can also be made to be disposable, and be provided preattached to the handpiece 300 as a kit. The quick change connector 88 of the inserter 10, as described herein, can be attached to the chuck 302 of the disposable handpiece 300. The disposable handpiece can be used to rotate the inserter tip 16 and the cutting edges 62, and push the inserter 10 into the bone 43 until the anchor braid 104 is fully inserted into the bone 43 (as described with respect to FIG. 33).

Generally, the following described and illustrated alternative all-suture anchor designs are configured to work with and be deployed by the anchor inserter described herein in the same manner as the other all-suture anchors, described above and illustrated herein. As with the other all-suture anchors, the alternative embodiments of the all-suture anchors can include a fibrous construct anchor body portion (or fibrous, braided or woven fabric-type structure such as a flexible web) and a suture or filament portion having a first end and a second end. The suture can pass through the filament in a number of ways (including woven, pass through a column, pierced through top and bottom, etc., as should be understood by a person of ordinary skill in the art in conjunction with a review of this disclosure). The fibrous construct can include a first state in which the fibrous construct is uncompressed and extends along the longitudinal axis of the filament when in an unfolded and pre-deployed condition; and a second state in which the flat fibrous construct is compressed and expanded in a direction perpendicular to longitudinal axis of the filament in a deployed condition (as discussed herein).

In accordance with one embodiment, the fibrous construct has an open elongated column/lumen extending from a first end to a second end; and the filament passes through and is positioned at least partially in the open column. In an embodiment, the filament is free to slide through the open column such that the filament can be removed from the open column from the first end of the fibrous construct and the second end of the fibrous construct. An embodiment of the fibrous construct can also be tubular in addition to having an open elongated column/lumen. The flat tape/fibrous construct may either be woven in situ directly onto the filament (e.g., a round section suture braid), or woven with an open column into which the round section suture braid may be later inserted. In particular, as seen in FIG. 38, a perspective view schematic representation of a soft all-suture anchor 400 in an unloaded (not loaded onto an installation device or inserter), pre-deployment configuration, according to an embodiment. The all-suture anchor 400 can include, but is not limited to, a flat fibrous construct 4 having a first end 4A, a second end 4B, and an open elongated column/lumen 6 having a first end 6A and the second end 6B (each of the first end 6A and the second end 6B of the open elongated column/lumen 6 can extend between or beyond the first 4A and second 4B ends of the flat fibrous construct). The open elongated column/lumen 6 can be woven along an axis that is parallel to or along a central axis of the flat fibrous construct 4, or can be woven along a path that is not parallel to the central axis. As shown in FIG. 38, the open elongated column/lumen is woven along the central axis.

Still referring to FIG. 38, a filament 2 is shown having a first end 2A and a second end 2B, and passing through and at least partially positioned in the open column 6. In an embodiment, the filament 2 is free to slide through the open column 6 such that the filament 2 can be removed from the open column 6 from the first end 2A of the fibrous construct 2 and/or the second end 2B of the fibrous construct 2. In accordance with an alternative embodiment, the filament is locked and not slidable through the open column 6.

Turning now to FIGS. 39A and 39B, there are shown side view schematic representations of an embodiment of the all-suture anchor 400 in the pre-deployment and post-deployment configurations. As described above, the all-suture anchor 400 contains at least two sections: at least one suture 2 with a first end 2A and a second end 2B; and an anchor body/fibrous construct 4 with a first end 4A and a second end 4B, and an open elongated column/lumen 6 extending from a first end 6A to a second end 6B, which is to form a portion of the anchor 400 that can increase in width, thickness and/or diameter and shrink in length as part of deployment.

As shown in FIG. 39A, the installation device (or inserter 10, as described herein above) in the pre-deployment configuration is provided. The all-suture anchor 400 is shown connected to the distal deployment end 804 of an installation device 800 (which can be an inserter of an embodiment described herein), which also includes a handle 802. The distal deployment end 804 and the all-suture anchor 100 are shown positioned in a bone hole 900 in cancellous bone 904 under the bone cortex 902. In order to deploy the all-suture anchor 400 (which can be connected to other tissue that needs to be brought into apposition to the bone, as should be understood by a person of ordinary skill in the art in conjunction with a review of this disclosure), the first end 2A and/or the second end 2B are pulled/tensioned in a direction away from the bone hole 400. The first end 2A and the second end 2B can be pulled/tensioned in a direction away from the bone hole 900 with or without the installation device 800 in place in the bone hole 900 (if installation device 800 is in place in the bone hole 900, it can act as a counter force to the tension force out of the hole 900 to assist with the deployment of the all-suture anchor 400).

As shown in FIG. 39B, the anchor body/fibrous construct 4 is shown "shortened" and "expanded" in the post-deployment configuration and locked in the bone hole 900, which can be additive to the increase due to pleats formed by the fibrous construct 4 (which may also be part of the fibrous construct 4). See also FIG. 39C. The all-suture anchor 400, and, in particular, the fibrous construct 4 takes advantage of Poisson's ratio (as described with respect to other anchors, above), which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. Although, it is the anchor body/fibrous construct 4 that increases in width, thickness and/or diameter at deployment, it should be understood that the suture 2 can also play a role in the deployment of the anchor 400 even though the suture 2 may remain free to slide in some embodiments, and non-slidable in others (at least at a particular position or point in use) in relation to the anchor body 4. The suture 2 helps to position, align and support the anchor body 4 (as should be understood by a person of skill in the art in conjunction with a review of this disclosure).

In other words, the anchor body/fibrous construct 4 has two primary functions. First, it becomes a base for the suture 2 to slide within (within the column/lumen 6). Second, when compressed and/or pleated during deployment, the anchor body 4 becomes more compact in one direction thereby expanding outwardly and increasing its overall width, thickness or diameter to create a retention capacity. This action of having the anchor body 4 change in shape to increase its overall width, thickness or diameter is a useful characteristic which may be used advantageously to secure the anchor 400 in a hole 900 or against a bony or soft tissue. It is this combination of the expanding anchor body 4 coupled with the suture 2 remaining slidable (in some embodiments; and non-slidable in others, at least at a particular position or point in use) in relation to the anchor body 4 that render embodiments of the present invention ideal for the reattachment of soft tissue to bone or soft tissue to soft tissue where it is desirable to pass sliding knots to secure a repair.

In one embodiment, an inventive configuration, structure, and resulting function of a soft all-suture anchor that utilizes a hybrid combination of soft implantable materials is provided. A hybrid soft all-suture anchor of an embodiment includes superior pull-out strength properties as compared to conventional soft all suture anchors. Embodiments of the present invention provide a better soft all-suture anchor for use in hard bone, due in part to a hybrid expanding component portion. These embodiments are also suitable for use in soft cancellous bone where there is a very thin or weak cortical layer. The hybrid all-suture anchor can include, but is not limited to, an expandable member/portion configured to increase in size from a first pre-deployed condition to a second deployed condition upon the application of an activator; and a filament having a first filament end and a second filament end, and positioned in contacting relation to the expandable member in the second deployed condition. The anchor can also include a flat fibrous construct having a first end and a second end, and wherein the filament passes through the fibrous construct. The flat fibrous construct includes a first state in which the flat fibrous construct is uncompressed and extends along the longitudinal axis of the filament when in an unfolded and pre-deployed condition; and a second state in which the flat fibrous construct is compressed and expanded in a direction perpendicular to longitudinal axis of the filament in a deployed condition. The structure, configuration, and functionality of the expandable member, and of the fibrous construct (when part of an embodiment), help to set and hold the anchor in the bone hole in a post-deployment condition. The expandable portion/member can be part of a hybrid all-suture anchor used with any filament portion (as described herein) only. The expandable portion/member can also be part of a hybrid all-suture anchor used with any filament portion and any fibrous construct portion (as described herein).

For example, referring to FIG. 40, a perspective view of a hybrid soft all-suture anchor 500 in a pre-deployment configuration, according to an embodiment is shown. The hybrid all-suture anchor 500 can include, but is not limited to, a flat fibrous construct 4 having a first end 4A, a second end 4B. A filament 2 is shown having a first end 2A and a second end 2B, and woven, threaded, or otherwise passing through the fibrous construct 4 at passing locations. See U.S. Pat. No. 9,826,971 for a further description of the structural aspects of the filament and fibrous construct, which is part of this example of the invention (as should be understood by a person of ordinary skill in the art in conjunction with a review of this disclosure).

In an embodiment, the filament 2 is free to slide through the fibrous construct 4 (and the expandable portion 3 when attached thereto) such that the filament 2 can be removed from the fibrous construct 4 from the first end 4A of the fibrous construct 4 and/or the second end 4B of the fibrous construct 4. In accordance with an alternative embodiment, the filament is locked and not slidable through the fibrous construct 4 and/or the expandable portion 3 (when attached to the expandable portion 3).

Turning now to FIGS. 41A and 41B, there are shown side view schematic representations of an embodiment of the all-suture anchor 500 in the pre-deployment and post-deployment configurations. As described above, the all-suture anchor 500 contains at least two sections: at least one suture 2 with a first end 2A and a second end 2B; and an anchor body/fibrous construct 4 with a first end 4A and a second end 4B, which is configured to form a portion of the anchor 500 that can increase in width, thickness and/or diameter and shrink in length as part of deployment. The all-suture anchor 500 also includes an expandable portion 3 which is configured to form a portion of the anchor 500 that can increase in size in the post-deployment configuration in response to an activator (as should be understood by a person of ordinary skill in the art in conjunction with a review of this disclosure).

As shown in FIG. 41A, the installation device (or inserter 10, as described herein above) in the pre-deployment configuration is provided. The all-suture anchor 500 is shown connected to the distal deployment end 804 of an installation device 800 (which can be an inserter, as described herein above), which also includes a handle 802. The distal deployment end 804 and the all-suture anchor 500 are shown positioned in a bone hole 900 in cancellous bone 904 under the bone cortex 902. In order to deploy the all-suture anchor 500 (which can be connected to other tissue that needs to be brought into apposition to the bone, as should be understood by a person of ordinary skill in the art in conjunction with a review of this disclosure), the first end 2A and/or the second end 2B are pulled/tensioned in a direction away from the bone hole 400. The first end 2A and the second end 2B can be pulled/tensioned in a direction away from the bone hole 900 with or without the installation device 800 in place in the bone hole 900 (if installation device 800 is in place in the bone hole 900, it can act as a counter force to the tension force out of the hole 900 to assist with the deployment of the all-suture anchor 500). In addition, an activator can be added to the anchor to cause the expandable portion to expand to a second size greater than the first pre-deployment size. In one embodiment, the activator is water.

As shown in FIG. 41B, the anchor body/fibrous construct 4 is shown "shortened" and "expanded" in the post-deployment configuration and locked in the bone hole 900, which can be additive to the increase due to pleats formed by the fibrous construct 4 (which may also be part of the fibrous construct 4). The all-suture anchor 500, and, in particular, the fibrous construct 4 takes advantage of Poisson's ratio (similarly, as discussed above), which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. Although, it is the anchor body/fibrous construct 4 that increases in width, thickness and/or diameter at deployment, it should be understood that the suture 2 can also play a role in the deployment of the anchor 500 even though the suture 2 may remain free to slide in some embodiments, and non-slidable in others (at least at a particular position or point in use) in relation to the anchor body 4. The suture 2 helps to position, align and support the anchor body 4 (as should be understood by a person of skill in the art in conjunction with a review of this disclosure).

In other words, the anchor body/fibrous construct 4 has two primary functions. First, it becomes a base for the suture 2 to slide within (within the column/lumen 6). Second, when compressed and/or pleated during deployment, the anchor body 4 becomes more compact in one direction thereby expanding outwardly and increasing its overall width, thickness or diameter to create a retention capacity. This action of having the anchor body 4 change in shape to increase its overall width, thickness or diameter is a useful characteristic which may be used advantageously to secure the anchor 500 in a hole 900 or against a bony or soft tissue. It is this combination of the expanding anchor body 4 coupled with the suture 2 remaining slidable (in some embodiments; and non-slidable in others, at least at a particular position or point in use) in relation to the anchor body 804 that render embodiments of the present invention ideal for the reattachment of soft tissue to bone or soft tissue to soft tissue where it is desirable to pass sliding knots to secure a repair.

Still referring to FIG. 41B, the expandable portion 3 is shown in the expanded second size, greater than the first smaller pre-deployment size, after exposure to the activator. The expandable portion expands greatly in volume when exposed to the activator, causing it to wedge in the bone hole 900 and lock the anchor 500 in place. In accordance with an embodiment, in order to tension the filament 2 to reattach soft tissue (not shown), the filament 2 can freely slide backward and forward through the fibrous construct 4 and through the expandable portion 3 (as may be necessary when connected to the expandable portion 3). In certain situations without the presence of fibrous construct 4, the free sliding filament 2 could potentially cut through the expandable portion 3 resulting in a less than optimum deployment of the all-suture anchor 500. As such, in some embodiments of the all-suture anchor 500 with or without the fibrous construct 4, a second short length of suture 2-1 could be wrapped or looped around the filament 2 (see FIG. 41C) to prevent sawing/cutting through the expandable portion 3 by the filament 2 when in contacting relation with the expandable portion 3.

Turning to FIG. 42, a side view digital photograph of an embodiment of the all-suture anchor of FIG. 40 in a post-deployment configuration after addition of an activator according to an embodiment is shown. As shown, the expandable portion 3 has increased in size to a second deployed structural condition (bone hole is not shown to illustrate the extent of expansion of expandable portion 3), and the filament 2 is positioned through and/or in otherwise contacting relation with the expandable portion 3.

Similarly with respect to the filament 2 and fibrous construct 4 described above and the embodiments shown in FIGS. 41A-C, the expandable portion 3 can be a part of any all-suture anchor described herein or otherwise including the all-suture anchor shown and described in U.S. patent application Ser. No. 16/033,616. The same structure and functionality of the expandable portion 3 described above and shown in FIGS. 41A-C can apply to these embodiments of an all-suture anchor (with and without the fibrous construct).

In accordance with an alternative embodiment of the present invention, an all-suture anchor insertion device 600 is provided as shown in FIGS. 43-45. The all-suture anchor insertion device 600 is configured to drill a bone hole in a desired anchor deployment location and deploy an all-suture anchor (which can include any all-suture anchor as discussed, referenced, described and/or illustrated herein) in the bone hole in one action with one device. In many procedures that involve soft tissue fixation in the extremities, a common issue is the surgeon losing the position of the hole they drilled in the bone for anchor deployment after removing the drill and guide. Additionally, during typical anchor insertion a drill guide must be held with one hand and the other hand is used to drill the pilot hole and insert the anchor. The all-suture anchor insertion device 600 incorporates a guide into the anchor which allows the procedure to be done single handed. The all-suture anchor insertion device 600 also reduces the time needed to install an anchor by combining the drilling and the anchor insertion steps into one. The uniqueness of the all-suture anchor insertion device 600 pertains, in part, to the use of an anchor driver rod 601 to drill a bone tunnel by oscillating it on a drill. The oscillating motion of the drill rotates the anchor driver rod 601 back and forth through. As the driver rod 601 oscillates, the tips of the fork 603-1 at the distal end of the device act as a drill bit to create a hole as a surgeon user pushes it into the bone. When the rod and anchor (positioned at the distal end of the device, not shown) have been inserted, the oscillation is stopped and the driver rod 601 is pulled out. The all-suture anchor is then set by pulling on the suture tails of the anchor, and/or adding an activator (as discussed herein).

In brief, as shown in FIGS. 43-45, the all-suture anchor insertion device 600 includes, but is not limited to, an anchor driver rod 601, a guide with a handle and a suture cleat 602, a sliding guide tip 603, a metal guide tube 604, and a single loaded all-suture anchor (not shown—preferably positioned on the distal end near the fork 603-1). The sliding guide tip 603 can be used to position an all-suture anchor before beginning to oscillate the device, and protects any surrounding tissues while the anchor is oscillating and being inserted.

A preferable functionality of the all-suture anchor insertion device 600 is to allow for anchor insertion with minimal steps from the surgeon in a method of using the same. In brief, the surgeon can connect a powered handpiece (not shown; e.g., as described above, or otherwise understood by a person of ordinary skill in the art in conjunction with a review of this disclosure) that has an equal oscillation mode to the back end of the inserter rod 601. Then holding the guide handle 602 and the powered hand piece the surgeon can position the sliding guide tip 603 at a location in bone and at an angle that they want to install the anchor. The surgeon can then turn on the oscillating mode of the hand piece, and push the inserter rod 601 into the bone (not shown). When the metal guide tube 604 becomes flush with the bone surface (and the distal end of the sliding guide tip 603 is flush with the distal end of the metal guide tube) oscillation can be stopped, the suture (not shown) is removed from the cleats, and the device is removed. The anchor can then be set by pulling on the suture tails, and/or and activator is added (as described herein and above).

Suture material, sutures, or filaments as the terms are used and described herein, can include monofilament or multifilament suture as well as any other metallic or non-metallic filamentary or wire-like material suitable for performing the function of a suture. This material can include both bioabsorbable and non-absorbable materials, and can be round, flat, or braided.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. An anchor inserter, comprising
   a cannulated inserter tube extending along a longitudinal axis having a proximal inserter end and distal inserter end;
   a cannulated suture tube extending through the cannulated inserter tube, the cannulated suture tube having a proximal suture tube and a distal suture tube end;
   an inserter tip attached to and extending distally from the distal inserter end, the inserter tip having a proximal tip end and a distal tip end;
   a suture anchor retention slot extending through the distal tip end, wherein the suture anchor retention slot comprises a straight portion connected to a curved portion that extends at an angle from the straight portion; and
   one or more features on the proximal tip end removably connected to one or more features on the distal inserter end.

2. The anchor inserter of claim 1, wherein the proximal tip end comprises a proximal tip tube and the distal suture tube end extends at least partially into the proximal tip tube.

3. The anchor inserter of claim 1, wherein one or more features on the proximal tip end are protrusions and the one or more features on the distal inserter end are slots.

4. The anchor inserter of claim 1, wherein the cannulated suture tube is substantially co-linear with the longitudinal axis.

5. The anchor inserter of claim 1, further comprising a quick change connector attached to and extending proximally from the proximal inserter end.

6. The anchor inserter of claim 5, wherein the quick change connector is an AO compatible quick chance connector.

7. An anchor inserter system, comprising:
   a cannulated inserter tube extending along a longitudinal axis having a proximal inserter end and distal inserter end;
   a cannulated suture tube extending through the cannulated inserter tube, the cannulated suture tube having a proximal suture tube end and a distal suture tube end;
   an inserter tip attached to and extending distally from the distal inserter end;

a suture anchor retention slot extending through the inserter tip, wherein the suture anchor retention slot comprises a straight portion connected to a curved portion that extends at an angle from the straight portion; and an anchor with a length of suture positioned therethrough extending through the suture anchor retention slot, such that the length of suture extends proximally along the inserter tip.

8. The system of claim 7, wherein the anchor is an anchor braid with the length of suture positioned through one surface of the anchor braid.

9. The system of claim 7, further comprising a plurality of passing locations along the anchor, wherein the length of suture is woven through the anchor at the plurality of passing locations.

10. The system of claim 7, wherein the length of suture extends into the distal suture tube end of the cannulated suture tube.

11. The system of claim 7, wherein the length of suture extends out from the cannulated suture tube at the proximal suture tube end and extends distally along an outer surface of the cannulated suture tube.

12. The system of claim 11, wherein the length of suture extends within an annular space between the cannulated suture tube and the cannulated inserter tube.

\* \* \* \* \*